(12) United States Patent
Pauli et al.

(10) Patent No.: US 8,175,817 B2
(45) Date of Patent: May 8, 2012

(54) RECIPROCAL SYMMETRY PLOTS AS A NEW REPRESENTATION OF COUNTERCURRENT CHROMATOGRAMS

(75) Inventors: Guido F. Pauli, Chicago, IL (US); J. Brent Friesen, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 930 days.

(21) Appl. No.: 11/961,026

(22) Filed: Dec. 20, 2007

(65) Prior Publication Data
US 2008/0201085 A1    Aug. 21, 2008

Related U.S. Application Data

(60) Provisional application No. 60/883,262, filed on Jan. 3, 2007.

(51) Int. Cl.
G06F 17/14    (2006.01)
G01N 31/00    (2006.01)

(52) U.S. Cl. .......................... 702/25; 708/400
(58) Field of Classification Search ........................ None
See application file for complete search history.

(56) References Cited

U.S. PATENT DOCUMENTS

| | | |
|---|---|---|
| 4,051,025 A | 9/1977 | Ito |
| 4,228,009 A | 10/1980 | Ito |
| 5,217,608 A | 6/1993 | Conway |
| 5,332,504 A | 7/1994 | Ito et al. |
| 5,354,473 A | 10/1994 | Ito et al. |
| 5,449,461 A | 9/1995 | Ito |
| 5,770,083 A | 6/1998 | Ma et al. |
| 6,503,398 B2 | 1/2003 | Ma et al. |
| 7,225,079 B2 | 5/2007 | Gjerde et al. |
| 2003/0054567 A1 | 3/2003 | Miyoshi et al. |
| 2008/0127720 A1 | 6/2008 | Pauli et al. |

FOREIGN PATENT DOCUMENTS

| | | |
|---|---|---|
| EP | 0 808 455 | 11/1997 |
| WO | WO 03/087807 | 10/2003 |

OTHER PUBLICATIONS

Walass (Acta Chemica Scandinavica, 1958, 12, 528-536).*

(Continued)

*Primary Examiner* — Larry Riggs
(74) *Attorney, Agent, or Firm* — Greenlee Sullivan P.C.

(57) ABSTRACT

Various methods for visualization of output from a liquid-liquid chromatographic instrument are provided. One or more analytes detected by a liquid-liquid chromatographic instrument are visualized by providing a data set comprising a plurality of data points corresponding to one or more analytes detected by the instrument, wherein the data points comprise at least one parameter related to a K-value or a parameter from which a K-value can be determined. A K-value is calculated for at least a portion of the data set, and at least a portion of those K-values transformed by a reciprocal transformation to generate output data having a transformed K-value, wherein the transformed K-value is a real number for all K undergoing the transformation, thereby ensuring that all analytes detected by the instrument are plotted in a single chromatogram. The output data is provided to a user. The output data may be used for instrument performance testing, design, calibration, or for selecting suitable solvent systems to detect analytes of interest.

17 Claims, 11 Drawing Sheets

OTHER PUBLICATIONS

Baderschneider et al. (2000) "Isolation and Characterization of Novel Stilbene Derivatives from Riesling Wine," *J. Agric. Food Chem.* 48:2681-2686.

Baderschneider et al. (2001) "Isolation and Characterization of Novel Benzoates, Cinnamates, Flavonoids, and Lignans from Riesling Wine and Screening for Antioxidant Activity," *J. Agric. Food Chem.* 49:2788-2798.

Berthod et al. (Jul. 2005) "Using the Liquid Nature of the Stationary Phase: The Elution-Extrusion Method," *J. Liq. Chromatogr. Relat. Technol.* 28(12-13):1851-1866.

Berthod, A. (Sep. 8, 2006) "Band Broadening Inside the Chromatographic Colum: The Interest of a Liquid Stationary Phase," *J. Chromatogr. A.* 1126(1-2):347-356.

Berthod et al. (2003) "Elution-Extrusion Countercurrent Chromatography. Use of the Liquid Nature of the Stationary Phase to Extend the Hydrophobicity Window," *Anal. Chem.* 75(21):5886-5894.

Berthod et al. (2005) "Alkane Effect in the Arizona Liquid Systems Used in Countercurrent Chromatography," *Anal. Bioanal. Chem.* 383:327-340.

Berthod et al. (Dec. 15, 2000) "Test to Evaluate Countercurrent Chromatographs: Liquid Stationary Phase Retention and Chromatographic Resolution," *J. Chromatogr. A* 902(2):323-335.

Berthod et al. (2007) "Elution-Extrusion Countercurrent Chromatography: Theory and Concepts in Metabolic Analysis," *Anal. Chem.* 79:3371-3382.

Berthod et al. (2004) "Determination of Liquid-Liquid Partition Coefficients by Separation Methods," *J. Chromatogr. A* 1037:3-14.

Berthod et al. (2000) "Countercurrent Chromatography: Fundamentally a Preparative Tool," *Adv. Chromatogr.* 40:503-538.

Cao et al. (Jun. 2003) "Separation of Dammarane-Saponins from Notoginseng, Root of *Panax notoginseng* (Burk.) F.H. Chen, by HSCCC Coupled with Evaporative Light Scattering Detector," *J. Liq. Chromatogr. Relat. Technol.* 26(9-10):1579-1591.

Cao et al. (Sep. 10, 1999) "Separation and Purification of Isoflavones from *Pueraria lobata* by High-Speed Counter-Current Chromatography," *J. Chromatogr. A* 855(2):709-713.

Chadwick et al. (2004) "Estrogens and Congeners from Spent Hops (*Humulus lupulus*)," *J. Nat. Prod.* 67(12):2024-2032.

Conway, W.D. (Jun. 2001) "An Indexing Scheme for Optimizing the Choice of Biphasic Systems for CCC 1," *J. Liq. Chromatogr. Relat. Technol.* 24(11-12):1555-1573.

Degenhardt et al. (2000) "Rapid Isolation of Malvidin 3-Glucoside from Red Wine by High Speed Countercurrent Chromatography (HSCCC)," *Vitis* 39:43-44.

Degenhardt et al. (2001) "Isolation and Purification of Isoflavones from Soy Flour by High-Speed Counter-Current Chromatography," *Eur. Food Res. Technol.* 213:277-280.

El Tayer e3t al. (1991) "Measurement of Partition-Coefficients by Various Centrifugal Partition Chromatographic Techniques—A Comparative-Evaluation," *J. Chromatogr.* 556:181-194.

Etter, L.S. (1993) "Nomenclature for Chromatography," *Pure Appl. Chem.* 65:819-872.

Foucault, L. (May 29, 1998) "Counter-Current Chromatography: Instrumentation, Solvent Selection and Some Recent Applications to Natural Product Purification," *J. Chromatogr. A* 808(1-2):3-22.

Friesen et al. (Oct. 2005) "G.U.E.S.S.—A Generally Useful Estimate of Solvent Systems for CCC," *J. Liq. Chromatogr. Relat. Technol.* 28:2777-2806.

Friesen et al. (2007) "Rational Development of Solvent System Families in Countercurrent Chromatography," *J. Chromatogr. A* 1151:51-59.

Friesen et al. (Mar. 2007) "Reciprocal Symmetry Plots as a Representation of Countercurrent Chromatograms," *Anal. Chem.* 79(6):2320-2324.

Gong et al. (Jun. 2003) "Selection of Aqueous Two-Phase Solvent Systems in CCC," *J. Liq. Chromatogr. Relat. Technol.* 26(9-10):1509-1520.

Gosse et al. (Dec. 2004) "Optimization of Active Saponin, Arganine C, for Microbicidal External Use," *J. Liq. Chromatogr. Relat. Technol.* 27(12):1947-1953.

Ito, Y. (Feb. 18, 2005) "Golden Rules and Pitfalls in Selecting Optimum Conditions for High-Speed Counter-Current Chromatography," *J. Chromatogr. A* 1065(2):145-168.

Ito et al. (1982) "High-Speed Preparative Countercurrent Chromatography with a Coil Planet Centrifuge," *J. Chromatogr.* 244:247-258.

Leo, A.J. (1987) "Some Advantages of Calculating Octanol Water Partition-Coefficients," *J. Pharm. Sci.* 76:166-168.

Li et al. (Oct. 12, 2001) "Preparative Isolation and Purification of Salidroside from the Chinese Medicinal Plant *Rhodiola sachalinensis* by High-Speed Counter-Current Chromatography," *J. Chromatogr. A* 932(1-2):91-95.

Long et al. (2006) "Development of an Efficient Method for the Preparative Isolation and Purification of Chlorophyll A from a Marine Dinoflagellate *Amphidinium carterae* by High-Speed Counter-Current Chromatography Coupled with Reversed-Phase High-Performance Liquid Chromatography," *Anal. Bioanal. Chem.* 386:2169-2174.

Lu et al. (Feb. 13, 2004) "Application of Preparative High-Speed Counter-Current Chromatography for Separation of Chlorogenic Acid from *Flos lonicerae*," *J. Chromatogr. A* 1026(1-2):185-190.

Oka et al. (1991) "Systematic Search for Suitable Two-Phase Solvent Systems for High-Speed Counter-Current Chromatography," *J. Chromatogr.* 538:99-108.

Oka et al. (Mar. 14, 2003) "Purification of Quinoline Yellow Components Using High-Speed Counter-Current Chromatography by Stepwise Increasing the Flow-Rate of the Mobile Phase," *J. Chromatogr. A* 989(2):249-255.

Pan et al. (2007) "Recent Progress in Countercurrent Chromatography," *J. Liq. Chromatogr. Relat. Technol.* 30:649-679.

Peng et al. (2006) "Efficient New Method for Extraction and Isolation of Three Flavenoids from *Patrinia villosa* Juss. By Supercritical Fluid Extraction and High-Speed Counter-Current Chromatography," *J. Chromatogr. A* 1102:44-50.

Peng et al. (May 13, 2005) "Preparative Separation of Isovitexin and Isoorientin from *Patrinia villosa* Juss by High-Speed Counter-Current Chromatography," *J. Chromatogr. A* 1074(1-2):111-115.

Salas et al. (2005) "Characterization of Pigments from Different High Speed Countercurrent Chromatography Wine Fractions," *J. Agr. Food Chem.* 53(11):4536-4546.

Schwarz et al. (2004) "Investigations on Anthocyanins in Wines from *Vitis vinifera* cv. Pinotage: Factors Influencing the Formation of Pinotin A and its Correlation with Wine Age," *J. Agric. Food Chem.* 52:498-504.

Shibusawa et al. (2006) "Three-Phase Solvent Systems for Comprehensive Separation of a Wide Variety of Compounds by High-Speed Counter-Current Chromatography," *J. Chromatogr. A* 1133:119-125.

Shibusawa et al. (2005) "Determination of log P-o/w for Catechins and their Isomers, Oligomers, and Other Organic Compounds by Stationary Phase Controlled High Speed Countercurrent Chromatography," *J. Liq. Chromatogr. Relat. Technol.* 28:2819-2834.

Shinomiya et al. (Mar. 2006) "Countercurrent Chromatographic Separation f Biotic Compounds with Extremely Hydrophilic Organic-Aqueous Two Phase Solvent Systems and Organic-Aqueous Three-Phase Solvent Systems," *J. Liq. Chromatogr. Relat. Technol.* 29(5):733-750.

Vallat et al. (1990) "Centrifugal Countercurrent Chromatography, a Promising Means of Measuring Partition-Coefficients," *J. Chromatogr.* 504:411-419.

Vidal et al. (2004) "Fractionation of Grape Anthocyanin Classes Using Multilayer Coil Countercurrent Chromatography with Step Gradient Elution," *J. Agric. Food Chem.* 52:713-719.

Zanatta et al. (2005) "Determination of Anthocyanins from Camu-Camu (*Myrciaria dubia*) by HPLC-PDA, HPLC-MS, and NMR," *J. Agric. Food Chem.* 53:9531-9535.

* cited by examiner

K Plot

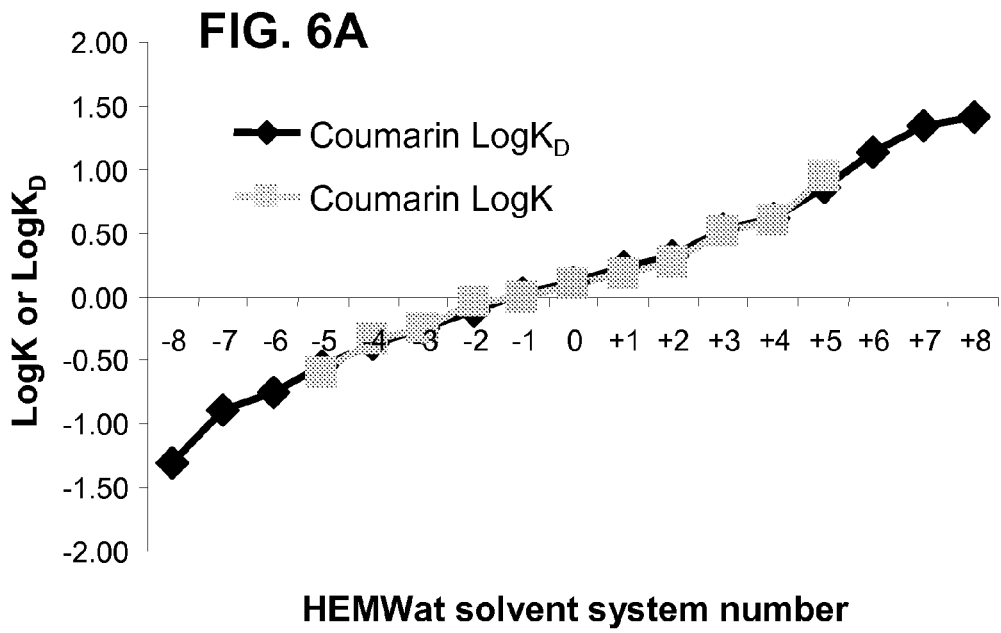
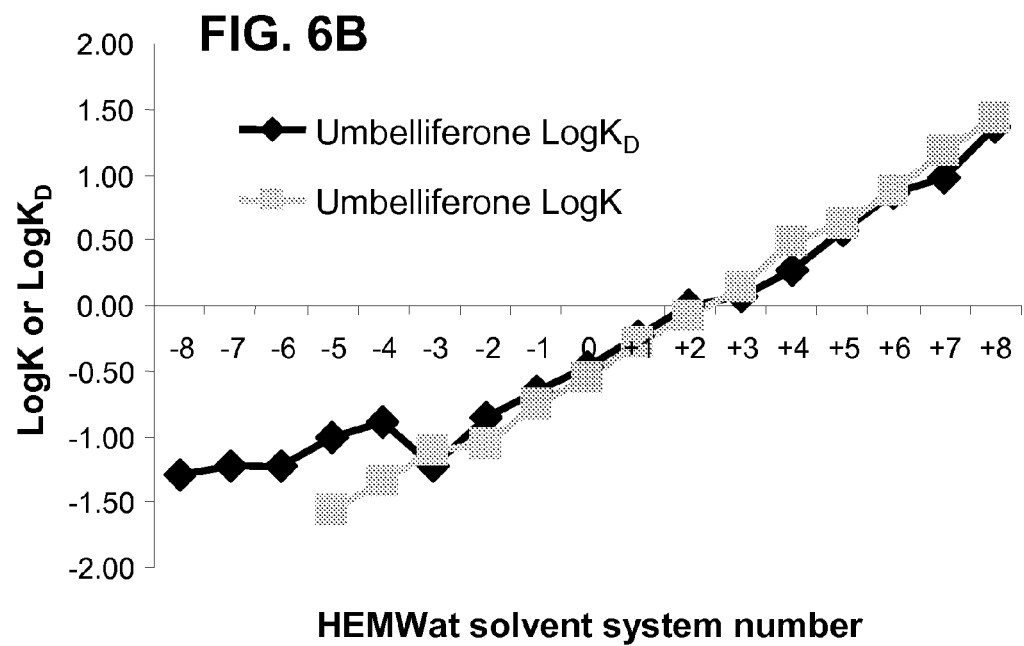

RECIPROCAL SYMMETRY PLOTS AS A NEW REPRESENTATION OF COUNTERCURRENT CHROMATOGRAMS

CROSS-REFERENCE TO RELATED APPLICATIONS

This application claims benefit of provisional patent application 60/883,262 filed Jan. 3, 2007 which is hereby incorporated by reference to the extent it is not inconsistent with the present disclosure.

BACKGROUND OF THE INVENTION

Chromatography is a well-characterized technique for isolating analytes, including often complex mixtures made up of a number of natural products. Such isolation is important to identify and further characterize compounds or impurities, and for use in a range of applications including assays to identify relevant candidate compounds based on activity, bioactivity or structure, and downstream applications related to pharmaceutical manufacture and chemical products. An important chromatographic technique is liquid-liquid chromatography that employs a two-phase immiscible solvent system for separating one or more analytes present as solutes in the system. For example, centrifugal partition chromatography (CPC) and countercurrent chromatography (CCC) are high-resolution separation techniques that can fractionate complex mixtures under mild conditions without adversely impacting the mixture constituents. The fractionation is based on the relative analyte solubility in the two immiscible phases.

The number of patents related to CCC provides an indication of the importance of this method in separating compounds (see, e.g., U.S. Pat. Nos. 4,051,025; 4,228,009; 5,217,608; 5,332,504; 5,354,473; 5,449,461; 5,770,083; 6,503,398; EP 0808455). Although there are many different CCC operating modes known in the art, these techniques all suffer from a common defect related to visualization of the data obtained from the instrument, commonly referred to as a chromatogram. These chromatograms are important because they provide a means for visually and quantitatively identifying the analytes detected by the instrument, and provide an indication as to the potential separation or "purity" of analytes as well as an assessment of the suitability of the solvent system to separate an analyte of interest. For example, if two analytes elute at a similar time, the separated compound will likely be a mixture of two different analytes. This presents a problem for applications requiring an isolated compound of high purity or that depend on the full resolution of analytes. Accordingly, it is important that the proper instrument and system related thereto be selected to provide maximum separation of the constituents that are in the mixture.

This selection is made difficult by the fact that CCC and CPC display conventional chromatograms, where it is impossible to make a meaningful comparison between different instruments, even when identical solvent systems and analytes are provided. The difficulty arises because conventional chromatograms are provided with instrument-dependent parameters plotted on the x-axis such as volume (see, e.g., Friesen and Pauli, J. Liq. Chrom & Related Tech. 28:2777-2806, 2005) or time (see, e.g., U.S. Pat. No. 5,770,083). Accordingly, it is not possible to compare the experimental results from one instrument with another. Further, it is difficult to verify whether an instrument is performing adequately or whether there are any calibration issues.

One means for facilitating instrument comparison is by providing chromatograms where instrument-independent parameters are plotted, such as by plotting a distribution constant (e.g., partition coefficient, partition constant, distribution coefficient, or any other nomenclature reflecting distribution between the immiscible phases), K, rather than a time or volume. An example of such a plot is provided in Friesen and Pauli (Anal Chem. (2007) 79(6):2320-4), where K is plotted on the x-axis and compared against conventional chromatograms.

One disadvantage of such a K-plot (and for plots using conventional parameters such as volume or time) relates to the inability of such plots to encompass all possible analytes, such as a plurality of analytes from a mixture having some analytes with a K-value that is about zero and with a value corresponding to infinity. Such a situation simply reflects the situation where an analyte is confined (e.g., dissolves) completely in only one of the two phases, corresponding to a K-value that is zero or infinity, or approaches one of these values. In addition, as the K-value increases, especially for those K values that are large, the peak width tends to increase. This increase in width can be misinterpreted as a decrease in resolution.

Although partition coefficients are known in the art of CCC (e.g., see U.S. Pat. No. 5,354,473), the methods and techniques presented herein provide a means for standardizing output results from any kind of liquid-liquid chromatographic instrument. Such standardization is valuable in a number of applications ranging from upstream instrument manufacture to downstream user experimental comparison, instrument calibration, solvent selection, and assessment of instrument performance. The methods disclosed herein provide improved means for assessing CCC and partition chromatography, resulting in increased reliability and confidence in the data obtained by such instruments, and can be integrated with any number of a wide range of existing and future-arising CCC and CPC instruments.

SUMMARY OF THE INVENTION

Conventional techniques that visualize the output from a liquid-liquid chromatographic instrument suffer a number of limitations that adversely impact a user's ability to make meaningful comparisons between chromatograms, instruments, assess instrument performance, and hinder the ability to visualize all possible analytes in a single chromatogram. Techniques and methods of the present invention overcome these limitations by providing specific transformation algorithms that transform data typically output by these instruments in a manner that permits all possible analytes to be displayed on a single chromatogram. Applications for such visualization methods include the ability to better and more reliably assess the result of the separation, instrument performance, provides a means for calibrating instruments, and allows for run-to-run and instrument-to-instrument comparisons and experimental validation, including assessment of solvent systems and selection of solvent systems for various analytes.

The methods provided herein present a platform for which all liquid-liquid based chromatographic instruments may be integrated. In particular, visualization of K-values permits run-to-run (e.g., different runs on the same instrument) comparisons, thereby facilitating method development and process optimization, instrument-to-instrument comparisons, calibration and performance assessment that is not available with conventional visualization techniques that rely instead on time and/or volume. In particular, use of those parameters is affected by instrument-specific variables so that a meaningful comparison of outputs between different instruments is not possible, particularly for instruments relying on different countercurrent separation techniques, for example. Instead, the present methods are universally applicable in that any liquid-liquid chromatographic instrument may be used, including partition-based instruments such as CPC and CCC instruments. In addition, the methods are applicable to any one or more operating modes or derivatives thereof, including future-arising liquid-liquid based chromatographic techniques and modes. The present invention provides a relatively simple means for standardizing instrument output, thereby facilitating instrument evaluation and output. This has a number of applications, including the ability of a user to better-select solvent systems, instrumentation, experimental collection parameters and the like depending on the analytes of interest. In addition, instrument manufacturers may use the methods provided herein to design and manufacture high-performance and reliable instruments. This, in turn, leads to an increase in instrument reliability and experimental certainty leading to better compound separation and collection.

In an embodiment, the invention is a method of visualization of one or more analytes detected by a liquid-liquid chromatographic instrument, such as a countercurrent or partition chromatographic instrument, for example. In particular, the visualization relates to chromatograms that display each detected analyte's liquid-liquid distribution ratio (e.g., the analyte concentration ratio between the two liquid phases, referred herein as K or K-value), and more particularly where the plurality of detected analytes are visualized as a transformed or an untransformed distribution ratio. Such visualization provides a number of advantages over conventional systems. For example, the visualization techniques presented herein facilitate a single x-axis chromatogram capable of displaying all possible analyte distribution ratios ranging from analytes that are exclusively soluble in the stationary phase and eluted only with the mobile phase (e.g., K=∞) to analytes that are exclusively soluble in the mobile phase (e.g., K=0). Conventional techniques including straight K-value plots, in contrast, cannot satisfactorily plot all possible analytes having a K-value that spans a range that includes zero and infinity.

In an embodiment, the analyte visualization is by providing a data set comprising a plurality of data points containing information related to a putative analyte detected by a chromatographic instrument. The data points correspond to an output of the instrument and particularly detection of an analyte, as analytes are extruded or eluted from the solvent-containing column by any modes known in the art or by any future-arising techniques. The data points have at least one parameter related to a K-value or a parameter from which a K-value can be determined. From the data points, a K-value is calculated for at least a portion of the data set, such as a K-value that is calculated for each of the analytes detected by the instrument. At least a portion of the calculated K-value is transformed by a reciprocal transformation (e.g., $K_T$ is proportional to $1/K^n$, where $n \geq 1$) to generate output data comprising a transformed K-value, wherein the transformed K-value is a real number for all K ranging from zero to infinity. "Transformed K-value" refers to at least a portion of the K-values from the data set undergoing a transforming operation. Accordingly, the term also refers to output data that contains both transformed and untransformed K-values, such as a transformed K-value wherein for K<M or K≦M $K_T$=K, and for K≧M or K≧M $K_T$ is derived from a transforming operation on K. In an aspect, this transformation occurs over a selected range of K values (for example, for all K>1), and the other range of K-values is either not transformed, or is transformed in a manner that is not a reciprocal transformation, such as $K_T$ is proportional to $K^m$, where $m \geq 1$. The output data is provided to a user. The output data is optionally used in any one or more of a number of applications ranging from analyte separation or characterization, instrument performance, instrument design and manufacture, calibration and the like.

In an aspect, any of the methods provided herein are for an instrument that is a CCC instrument or a partition chromatography instrument. The methods are not restricted to any particular instrument or operating mode. Some specific examples of various operating modes include, but are not limited to, normal mode; dual mode; EECCC (elution-extrusion CCC); BECCC (back extrusion CCC); gradient mode; and pH zone refinement mode.

In another embodiment, the K-value corresponds to a liquid-liquid distribution ratio ($K_D$) value, which may be calculated as known in the art from the equation: $K=(V_R-V_M)/V_S$. Each of $V_R$, $V_M$, and $V_S$ are the experimentally measureable or calculated parameters of retention volume ($V_R$), mobile phase volume ($V_M$), and stationary phase volume ($V_S$). These, and other parameters of interest may be contained in the data set (e.g., as data points). For example, the various volume parameters may be provided by the data set (e.g., directly measured), or be calculated as known in the art from one or more data points in the data set.

In an embodiment, the visualization of any of the methods is provided to a user in a graphical form, such as on a monitor, screen, or permanently affixed to a hard-copy printout. The graphical from is obtained by plotting onto a X-Y coordinate system the transformed K-value and untransformed K-value as a x-coordinate and plotting a parameter related to an analyte relative amount as a y-coordinate on the X-Y coordinate system (e.g., an optical property such as absorbance or transmission, or other indicator of amount such as radioactivity). The resultant plot forms a reciprocal symmetry (ReS) plot for all analytes detected by the instrument. In contrast to conventional methods, such a plot is capable of displaying all possible analytes, irrespective of their K-value. In conventional visualization methods, there is difficulty in displaying analytes that are confined to one of the liquid phases (e.g., having a K-value corresponding to infinity). Furthermore, the ReS plot provides good separation and spacing from other analytes and can be employed to assess performance of various chromatographic instruments and for instrument calibration, for example.

In another aspect, any of the methods disclosed herein relates to a specific equation for performing the reciprocal transformation step. In general, the reciprocal transformation yields a transformed K-value that is proportional to an inverse of the calculated K-value. One specific example is $K_T=1/K$, where $K_T$ is the transformed K-value and K is the K-value calculated from the data set. Such a reciprocal transformation ensures that for very large K, $K_T$ remains readily plottable. To avoid $K_T$ becoming large for very small K, this transformation step is performed for those K that are above a user-selected or automatically selected reciprocal transformation cut-off value, e.g., for cut-off values that are about 1, between about 0.001 and 1000, or less than about 100. A cut-off value of 1 ensures that the range of all possible untransformed values equals the range of all possible transformed values (e.g., a range of 1:0→1 (untransformed); and 1→0 (transformed)). In an aspect, this cut-off value is referred to as a symmetry midline, "M". M provides a means for "balancing" the output data between either side of the M value and such plots are referred to as Shifted Reciprocal Symmetry (ReSS).

In an embodiment, the transformation is by the transforming operation:

$$x = 2M - 1/K;$$

$$x = 2M - M^2/K;$$ or more generally:

$$x = aM - b/K;$$

where M is the symmetry midline, K is the calculated K-value, and x (e.g., $K_T$) is the transformed K-value that is part of the output data provided to a user. The variables a and b are optionally selected depending on the system (e.g., solvent system and analytes), where a is greater than or equal to zero, and b is greater than zero. In an aspect $0.001 \leq a \leq 1000$ and $0.001 \leq b \leq 1000$. In another aspect $b = cM^2$ where c is a symmetry midline factor used to shift the ReS plot, and $c > 0$.

In particular, selection of an M value that is not one (1) effectively "shifts" the ReS plot. Accordingly, such a process is referred to as a ReSS plot.

In another aspect, for K less than M, the K-value is not transformed (e.g., x=K) so that the transformation of calculated K corresponds to a range of K-values that are greater than or equal to M. In an embodiment, M is selected to have a value that corresponds to an optimum resolution of analytes (e.g., a sweet spot of the instrument), such as, for example $0.25 < M < 16$, or $0.1 < M < 25$. Accordingly, in an embodiment the process provides automated selection of an M-value that in turn depends on the spectrum of K-values for the solvent/analyte system. The explicit range of optimum resolution depends on the specific analyte and solvent system employed, but can be determined by evaluating the spectrum of K-values for the detected analytes, such as a region wherein about the middle, 25%, 50% or 70% of K-values reside, or alternatively, at the analyte having the K-value median. Optimum resolution range further refers to the range (in terms of volume, time, or K) of a CCC or CPC instrument where the resolution of pairs of analytes is the best balance of separation time, separation quality, and resources required for satisfactory separation. Separation quality can be quantified in terms of the purity and/or amount of the separated analytes. Such a definition provides a means for automatically selecting M based on the detected analytes.

Alternatively, M optionally has a user-selected value that is selected from a range that is greater than or equal to 0.001 and less than or equal to 1000, or any value therein, so long as the output data maintains a generally reciprocal symmetry relationship.

The visualization is provided to the user as output data by any method capable of conveying useful information. For example, for those applications where real-time evaluation is desired, the output data may be displayed on a monitor for real-time viewing. Of course, output data may be digitally stored on an electronic medium for subsequent analysis. Another useful system involves a hard-copy print-out of the output data. Alternatively, a plurality of these output data visualization means are used (e.g., real-time display as well as electronic storage media of the data set or output data). The methods provided herein can be used with a real-time chromatography experiment or performed on a "raw" or partially transformed data set obtained from a previous (e.g., stored data set) or non-real-time experiment.

The data output by the methods provided herein have many useful applications. For example, separation performance, instrument performance, design, assessment and/or calibration. In an embodiment where instrument performance analysis is desired, the steps for visualization of the analytes may be repeated for any number of the same or different chromatography instruments. Similarly, for applications where the best separation is desired for a given instrument, the methods provided herein are employed by visualizing a variety of instrument and solvent system parameters for that instrument. In an embodiment, each of the steps of the visualization method is repeated to obtain a second output data, such as from another chromatographic instrument or from the same instrument but from a second experimental run of detecting the same set of analytes. The second output data is compared to the first output data to determine an instrument performance parameter for at least one instrument. In another aspect, the instrument performance parameter is selected from one or more of analyte peak sharpness; analyte peak magnitude; absence or presence of one or more analyte peaks; an analyte K-value; analyte peak symmetry; peak resolution; and solvent system parameter such as volumes, flow-rates, polarity. Methods provided herein are used to also assess solvent systems, including selecting solvent systems that provide improved data output, resolution and reliability by evaluating the output data ReS and ReSS plots, for example.

In another embodiment, the analytes introduced to the instrument are from one or more reference standards. With respect to calibration and performance assessment, it is useful to provide a plurality of reference standards, including a plurality of well-characterized analytes that span a spectrum of interest (e.g., polarity; hydrophobicity; lipophilicity, structural diversity (such as a structurally-diverse set of natural products, derivatives of chemicals or chemical scaffolds), biological activity, etc. One example are analytes that are one or more components of a GUESSMix standard, including but not limited to every component of the GUESSMix standard (see FIG. 5, or a subset thereof, such as the example provided in FIG. 2). The reference analyte need not be a component of the GUESSMix standard, but instead is any material that can be used as a basis for comparison, such as an isolated and purified material. Solvent systems may be selected as provided in Ser. No. 11/876,545 (156-07) filed Oct. 22, 2007 (Pauli et al.), incorporated by reference herein, and specifically for analytes, solvent systems and selection thereof.

In an aspect, the invention is a method of calibrating chromatographic partition chromatography instruments, CCC, or CPC instruments. This is achieved, in an embodiment, by providing a standardized ReS or ReSS plot by any of the methods wherein the analyte comprises one or more reference analytes. The output data for such a reference analyte procedure is referred to as a "reference output data". The reference output data is compared against the output data, wherein the output data is from the instrument to-be-calibrated. This comparison is used broadly to refer to identifying one or more parameters of interest, and then evaluating that parameter for the output data and comparing it against the reference-value parameter from the reference output data. One or more instrument parameters are selectively adjusted so that the parameter from the output data substantially corresponds to the reference parameter from the reference parameter. Instrument parameter is used broadly to refer to any parameter that affects data output and accordingly includes hardware or software-type parameter. Hardware refers to a physical change in instrument configuration such as during instrument manufacture including, but not limited to, quality (e.g., tolerance, material purity), dimensions, underlying separation mode or technique, materials, dimensions and mechanics of the CCC/CPC instrument (e.g., centrifuge mechanics for centrifuge-based devices), and for CCC: winding, dimensions and material of the coils, dimensions and material of a container that constrains the liquid-liquid solvent system, and for CPC: cell and flowpath design, materials, dimensions; volumes (active, dead volumes, mobile and stationary volumes and ratios thereof). With respect to software-type parameters, examples include manipulation of parameters after the instrument is manufactured, including but not limited to, spinning (e.g., centrifugation) rate, flow rate, injection technique, selection of two-phase solvent system, pressure regulation, temperature, etc. "Substantially corresponds" refers to a parameter value that is within about 20%, 10% or 5% of the reference. Examples of output data parameters of interest for calibration include analyte peak sharpness; analyte peak magnitude; absence or presence of one or more analyte peaks; an analyte K-value; analyte peak symmetry; peak resolution; K-value and parameters related thereto such as volumes, flow-rates, etc.

In an aspect, the K-value is calculated from values stored as data points, such as by the equation:

$$K=(V_R-V_M)V_S$$

wherein $V_R$ is retention volume, $V_M$ is mobile phase volume, and $V_S$ is stationary phase volume, where each of those volumes is experimentally known, measured or calculated. Accordingly, if during calibration or performance assessment, there is a significant deviation in K, each of one or more parameters upon which the K-calculation is based may be scrutinized and further investigated (or the instrument identified as "deficient" or sub-standard for that solvent system/analyte experiment).

In another embodiment, the invention provides various methods for evaluating a performance parameter of a countercurrent chromatography instrument. The performance parameter may be evaluated by introducing one or more reference analytes, optionally one or more of a GUESSmix reference standard, to the instrument. The instrument detects at least one of the reference analytes. A K-value is determined for at least one reference analyte, and the K-value transformed by any of the transforming operators disclosed herein. In an embodiment, the transformed K-value is defined as: $K_T=K$, for all K less than or equal to M, and $K_T=aM-b/K$ for all K greater than or equal to M, wherein a is greater than or equal to 1; b is greater than or equal to 1 or b is equal to $cM^2$; wherein c is greater than 0; M is greater than 0. In an aspect, the value at $K_T=M$ is selected as K. Alternatively, the value at $K_T=M$ is selected in accordance with the transformation equation. The transformed output data is compared to a provided a standardized $K_T$ data set, wherein the standardized set is from the same one or more reference analytes. Data set comparison refers to an evaluation of a spectrum of $K_T$ to ensure individual analytes are detected, and their relative $K_T$ values, for example. Such comparison techniques are known in the statistical arts and includes any of a variety of summation of deviation values over the spectrum or a range thereof, deviation of individual peaks in the spectrum, difference in peak shapes, separation and/or magnitude, and any one or more parameters in the chromatography system used to calculate K-values (e.g., volumes, flow rate, solvents, analytes).

In another embodiment, any of the methods described herein use any one or more reference analytes from a GUESSmix reference standard. The standardized data set is optionally from a second (e.g., a different) instrument or column used in the chromatography, but with the same solvent and analyte system. Alternatively, the standardized data is from the same instrument or column, but from a different experimental run (e.g., such as a standardized data set provided by the column manufacturer), or for comparing runs in normal phase and reversed-phase modes. In embodiments, the performance parameter is selected from the group consisting of analyte peak sharpness; analyte peak magnitude; absence or presence of one or more analyte peaks; an analyte K-value; analyte peak symmetry; peak resolution; solvent system parameter; analyte loading; and analyte purity.

DETAILED DESCRIPTION OF THE INVENTION

Figure 1:
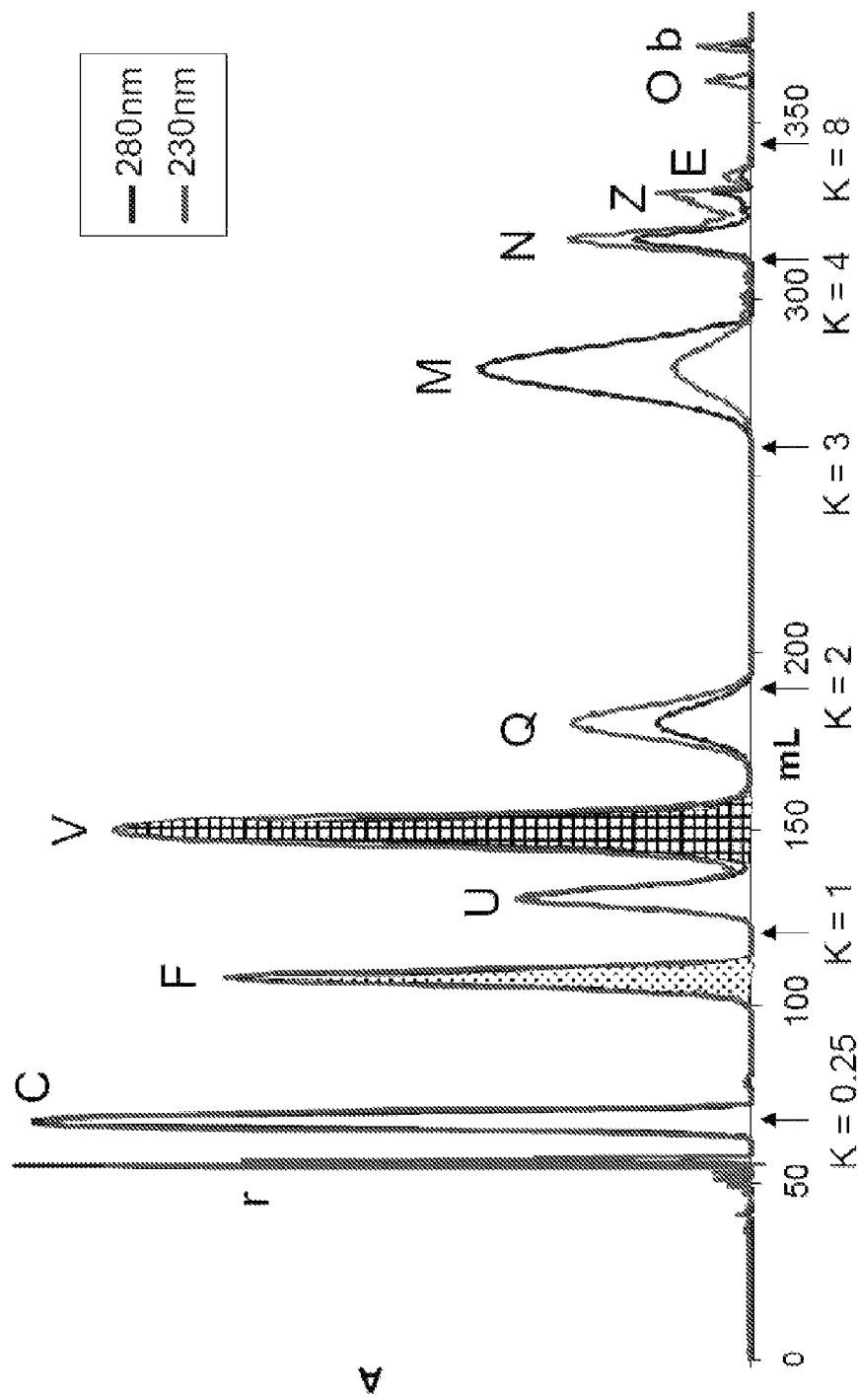
FIG. 1. HSCCC separation of selected GUESSmix compounds in hexane/ethyl acetate/methanol/water 4:6:4:6 for two different wavelengths (230 nm and 280 nm). The column exhibited 58% retention of stationary phase. Elution-extrusion was begun at 254.5 mL. K-values of 0.25, 1, 2, 3, 4, and 8 were calculated to correspond to 67.5, 120, 190, 259, 311, and 343 mL respectively. The output data is displayed as a conventional retention volume plot.

"Visualization" is used broadly herein to refer to any means for conveying information about output data in a useful manner to a user, and in particular transformed K-values, from a chromatographic instrument. For example, the visualization may be by display on a monitor, hard-copy print-out on paper or electronically stored on a computer-readable medium. The visualization may be temporary (e.g., on a display connected to the chromatographer) or permanent (e.g., on a print-out or stored in an electronic medium). In one embodiment, the visualization refers to display of output data in a graphical form, e.g., chromatographic, where peaks correspond to analytes.

"Analyte" refers to a substance which is to be detected, separated, purified or analyzed during chromatography. Analyte is used broadly to refer to a sample containing one or more unknown analytes, such as a natural product, for example. Alternatively, analyte may refer to one or more reference analytes, such as an isolated and purified reference analyte having known properties such as polarity, K-value in one or more solvent systems, and other parameters of interest. Introduction of such one or more reference analytes, in combination with the K-plots of the present invention, permits run-to-run comparisons, instrument-to-instrument comparisons, instrument calibration and performance, solvent system selection, and the like.

"Liquid-liquid chromatography" refers to partition equilibrium of an analyte between a two-phase liquid system, such as a liquid stationary phase and mobile liquid, and specifically includes countercurrent chromatography. One example of a liquid-liquid chromatographic partition chromatography instrument is countercurrent chromatography. Countercurrent chromatography is a well characterized technique (see, e.g., U.S. Pat. Nos. 5,770,083, 5,449,461, EP 0808455, WO 03/087807). "Liquid-liquid chromatographic partition chromatography instrument" refers to those instruments that rely on liquid-liquid chromatography to detect, separate and or analyze one or more analytes introduced to a column containing the biphasic liquid solvent system. The instrument may further utilize any technique known in the art that provides elution/extrusion of materials from a liquid solvent including, but not limited to, counter-current chromatography and one or more modes of normal mode, dual mode, EECCC, BECCC, gradient mode; and pH zone refinement mode, for example.

Examples of various solvent systems, and methods related for various mapping, characterization, and solvent selection techniques, are provided in U.S. patent Ser. No. 11/876,545 (156-07) filed Oct. 22, 2007 (Pauli et al.), which is hereby specifically incorporated by reference for solvent families, selection of such solvent systems and solvent family mapping as applied to chromatographic methods employed herein.

"Data set" refers to measured or detected parameters from the instrument over the course of an experiment, and comprises a plurality of data points. For example, with respect to the liquid-liquid chromatographic partition chromatography instruments used herein, the data set may include one or more data points that correspond to a volume parameter ($V_R$, $V_M$, $V_S$), time, and an indication of relative amount of analyte, such as optical absorbance or transmission, or radioactivity, for example. Data set may also include instrument or run-specific variables, such as flow rate, correction factors, column volume, dead volume and any other parameters of interest for use in calculating a K-value for an analyte or for instrument comparison, validation, performance assessment or calibration.

As used herein, K is a distribution constant or partition coefficient that is a measure of how a compound or analyte distributes between two immiscible solvent phases, and can have any value ranging from zero to infinity. In an aspect, K is referred to as $K_D$ and can have extreme values of infinity or zero, representing the situation where a compound or analyte is restricted to one of the two immiscible solvent phases. Depending on the particular definition of K, K is calculated in one of any manner of methods, depending on the parameters contained in the data set. For example:

$$K=(V_R-V_M)V_S$$

The correct or generally accepted representation for the distribution constant (K) in countercurrent chromatography, such that $V_R=V_M+KV_S$, is still under consideration. The specific representation for K in the methods disclosed herein is not critical, so long as the value adequately reflects the distribution of the compound between the immiscible solvent phases in the system. Examples of different representations for a distribution constant recognized in the art include $K_C$, $K_D$, D, and K, for example, each having advantages and disadvantages, depending on the system.

In the 1993 IUPAC nomenclature for chromatography section, the distribution constant ($K_c$) is defined as the analytical concentration of a component in the stationary phase divided by its analytical concentration in the mobile phase (Ettre, L. S. *Pure Appl Chem* 1993, 65, 819-872). The term "analytical concentration" may be understood to mean the total amount of a component per unit volume, regardless of its chemical form. Despite the apparent appropriateness of the 1993 IUPAC nomenclature, the notation $K_c$ is very rarely used in CCC literature.

The notation $K_D$ is commonly used in CCC literature. (Berthod, A.; Billardello, B. Advances in Chromatography, Vol 40 2000, 40, 503-538; Berthod, A. Countercurrent Chromatography: The Support-Free Liquid *Stationary Phase*; Elsevier, 2002; Berthod, A.; Ruiz-Angel, M. J.; Carda-Broch, S. *Anal. Chem.* 2003, 75, 5886-5894.) The current IUPAC Compendium of Chemical Terminology defines the partition ratio ($K_D$) as the ratio of the concentration of a substance in a single definite form, in the extract to its concentration in the same form in the other phase at equilibrium, e.g. for an aqueous/organic system (IUPAC Compendium of Chemical Terminology, Electronic version, world wide web page: goldbook.iupac.org/P04440.html). CCC requires a more general definition for liquid-liquid distribution since some solutes (weak acids, for example) may exist in multiple forms as a result of association or complex formation, while other solutes may remain as unassociated single species.

The current IUPAC Compendium of Chemical Terminology defines the distribution ratio, (D) in liquid-liquid distribution, as the ratio of the total analytical concentration of a solute in the extract (regardless of its chemical form) to its total analytical concentration in the other phase (IUPAC Compendium of Chemical Terminology, Electronic version, world wide web page: goldbook.iupac.org/D01817.html). Despite the apparent appropriateness of D in IUPAC nomenclature, the notation D to the best of our knowledge is not used in CCC literature.

The distribution constant (K) has been used extensively in CCC literature (Ito, Y. *J. Chromatogr. A*. 2005, 1065, 145-168; Friesen, J. B.; Pauli, G. F. *J. Liq. Chromatogr. Rel. Technol.* 2005, 28, 2777-2806; Conway, W. D.; Petroski, R. J. *Modern Countercurrent Chromatography*; American Chemical society, 1995.). Despite the traditional use of K in CCC literature, the term has not been officially adopted by IUPAC nomenclature. However, in the current IUPAC Compendium of Chemical Terminology, the distribution constant in chromatography (no symbol included) is defined as the concentration of a component in or on the stationary phase divided by the concentration of the component in the mobile phase. (IUPAC Compendium of Chemical Terminology, Electronic version, world wide web page: goldbook.iupac.org/D01814.html). The analytical condition used here refers to the total amount present without regard to the existence of various forms.

The methods presented herein do not depend on a specific notation, or require the use of a notation that is ultimately appropriate for countercurrent chromatography. The notation K is used herein simply because it: (i) reflects the majority of CCC literature, (ii) does not explicitly contradict current IUPAC nomenclature, (iii) does not discount the possibility for the IUPAC team of the International Society for Countercurrent Chromatography (ISCCC) to develop a consistent, possibly new "$K_{ccc}$" nomenclature. Any such developed and/or adopted $K_{ccc}$ nomenclature may be used in any one or more methods disclosed herein.

"Transforming" refers to an operation on the K-value to obtain a transformed K-value so that all possible K-values are capable of being expressed as a real number (e.g., $0 \leq K < \infty$), thereby facilitating, for example, a ReS graphical representation of all possible experimental K-values. This is particularly useful for graphical plots on an X-Y coordinate system. This transformation optionally occurs over a portion only of K-values, such that one range of K-values is untransformed, and a second non-overlapping range of K-values is transformed. A specific transformation equation is not crucial; instead the particular transformation may be tailored to the detected K-values or K-values calculated from the chromatographic data set. Furthermore, a user-selected or automatic selection of a transformation cut-off may occur so that the resultant visualization is balanced (referred to as ReSS plot). Such a balanced visualization facilitates relatively simple and easy comparisons, whereas unbalanced visualization can make qualitative analysis more difficult.

"Real time" refers to visualization of an output data of an experiment that is ongoing. As understood in the art, there may be some delay time related to algorithmic transformations, the actual visualization, and the like. The term is meant to distinguish from those experiments that are analyzed post-acquisition, where there is a substantial delay in the visualization from when the analytes were introduced to the instrument.

"Parameter" has a number of different meanings, depending on the context. For example, "instrument performance parameter" refers to a property of the instrument that may be adjusted to provide better-quality output data. The term includes hardware (e.g., instrument design) as well experimental-specific parameters such as flow-rates, solvent selection, volumes, etc. Parameter, in the context of describing data output, refers to the data-specific parameters such as peak symmetry, K-values, and any other quantitative or semi-quantitative parameters that describe or are calculated from such data. Parameter, in the context of a solvent system, refers to the type of solvent system employed, such as the make-up of each of the two phases and properties related thereto such as polarity, for example.

Figure 5:
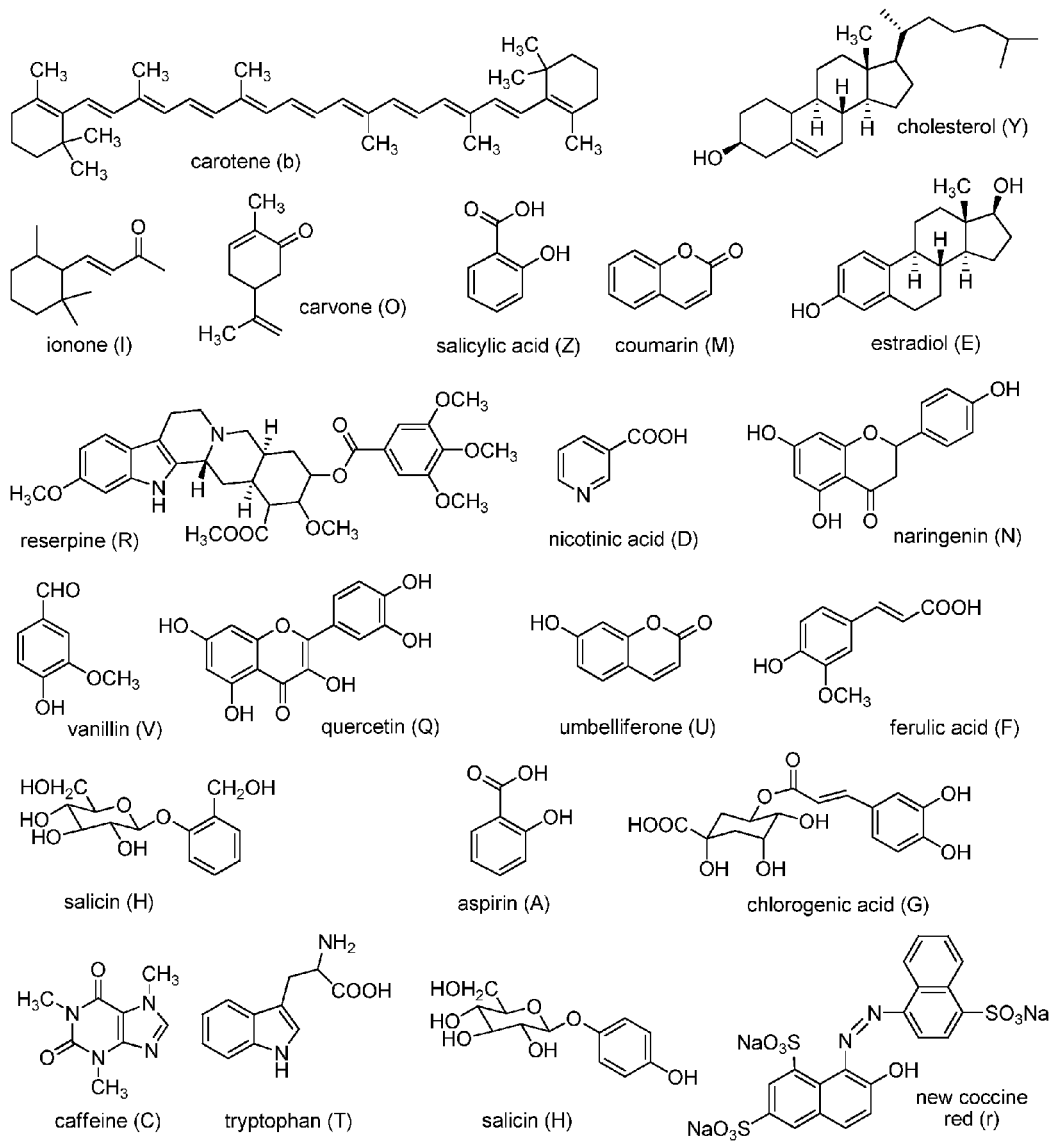
FIG. 5 GUESSmix compounds and their single letter abbreviations useful as reference standards for calibration and performance assessment for chromatographic columns and instruments.

"GUESSmix reference standard" refers to the list of compounds in FIG. 5, or any one or more individual components thereof. "Reference analyte" refers to any compound used to validate, calibrate or assess instrument performance. For example, any one or more of the compounds in the GUESSmix standard may be a reference analyte.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

EXAMPLE 1

Reciprocal Symmetry Plots

Traditionally, chromatograms in countercurrent chromatography (CCC) have been plotted with retention volume or time on the x-axis. However, the distribution constant (K) is a more appropriate, reproducible value for the x-axis, because it is a physicochemical property of a particular analyte in a particular solvent system. Therefore, K is independent of both the total column volume and the stationary phase volume ratio ($S_F$) of the column. Going one step beyond simple K plots, the Reciprocal Symmetry (ReS) plot, with K and 1/K positioned on either side of a line of symmetry on the x-axis, represents all K-values, zero to infinity. Based on experimental evidence, using a mixture of CCC reference standards, the ReS plot demonstrates both the invertible and "symmetric" nature of CCC, a consequence of the exchange of the mobile and stationary phases by reversing the direction of the flow and the symmetry of the liquid-liquid partitioning process between two immiscible phases, respectively. Moreover, the interval of optimal resolution can be centered on the ReS plot to focus on K-values of interest, establishing the Reciprocal Shifted Symmetry (ReSS) plots in CCC. Improved representation of peak shape across the whole CCC polarity range is an added advantage of ReSS plots over both K and classical retention volume plots.

Countercurrent chromatography (CCC) is a separation technique that distributes analytes between two immiscible liquid phases in order to effectuate their separation.[1-3] The absence of a liquid/solid or gas/liquid interface allows for the maximizing of surface interactions between the two chromatographic phases through continuous mixing and settling. For this reason, CCC is a high-resolution separation technique, capable of fractionating complex mixtures under very mild conditions, and only based on their relative solubility in the two immiscible phases. CCC has the added advantage that it can be reproducibly scaled up by simply increasing the size of the column.[4]

Due to the exclusive involvement of liquids (solvents), it is widely accepted that CCC permits the complete recovery of all analytes introduced to the column. The retention volume of an analyte follows the classical elution equation (1):

$$V_R = V_M + K V_S \tag{1}$$

The ratio of the analyte concentration in the stationary phase to its concentration in the mobile phase determines the analyte's distribution constant, K (as discussed herein, K may also be represented by $K_D$ or $K_C$. The equation shows the relationship between the K-value and the experimentally measurable parameters of retention volume ($V_R$), mobile phase volume ($V_M$), and stationary phase volume ($V_S$). However, if a column is eluted only with mobile phase, it will theoretically take an infinite amount of time for an analyte that is exclusively soluble in the stationary phase ($K=\infty$) to exit the column.

In practice, one way of overcoming this limitation and to ensure that all the analytes are recovered is to completely extrude the column contents (both stationary and mobile phase) at a defined point of the elution stage of the chromatography. This method has recently been developed by Berthod and coworkers, who described the basic theory and introduced the term of elution-extrusion CCC (EECCC).[5-7] Extrusion of the stationary phase is achieved by switching the supply of flowing liquid from the mobile phase to the originally stationary phase, while maintaining the centrifugal force through continued rotation (conditions found in modern CCC instrumentation). The calculation of K-values in EECCC chromatograms can be performed by applying two equations. During the classical mode (CM) elution stage, the following equation (2) describes the K-value:

$$K=(V_R-V_M)/V_S \quad (2)$$

Upon initiating extrusion at volume $V_{CM}$ (classical mode elution volume) by switching the liquid phase supply, elution continues to occur for the volume of the mobile phase $V_M$. Thus, equation (2) yields the K-values of all those analytes that actually elute, which occurs during the volume $V_{CM}+V_M$. In the subsequent extrusion stage, which is characterized by the effluent being exclusively the originally stationary phase, K-values are calculated by the following equation (3).[8]

$$K=V_{CM}/(V_{CM}+V_C-V_R) \quad (3)$$

The point at which extrusion is begun can be adjusted to optimize the resolution of target analytes in a minimum amount of time. When $V_R$ is equal to $V_{CM}+V_C$ ($V_C$ is the total volume of the column), all analytes will have exited the column. The elution-extrusion concept, therefore, allows K-values to be calculated for all analytes, including those with K-values approaching infinity.

The methods disclosed herein are capable of including the complete range of K-values on the x-axis of a single CCC chromatogram. The newly introduced method of reciprocal symmetric (ReS) plots goes two steps beyond the widely used volumetric plots of CCC chromatograms, and one step beyond proposed plots of K.[9] This concept has three advantages over currently used routine CCC plots: (i) it integrates elution and extrusion phases in the chromatograms; (ii) it allows coverage of all K-values, zero to infinity; and (iii) it provides a new means for the representation of symmetry in CCC, which represents an underlying principle in liquid-liquid partition-based chromatography.

Instrumentation: A J-type instrument (Model CCC-1000; Pharma-Tech Research Corporation, Baltimore, Md., USA) containing a self-balancing centrifuge rotor equipped with 3×40 mL coils is utilized for high-speed countercurrent chromatography (HSCCC). The coils were wrapped with 1.6 mm internal diameter of PTFE (Teflon) tubing. The rotation of coil assembly relative to the coil winding situated the head at the periphery position (for a more complete explanation of this phenomenon see the Supporting Information). The revolution radius of the distance between the holder axis and central axis of the centrifuge (R) is 7.5 cm. The β ratio ($β_r$) varied from 0.73 at the head terminal to 0.47 at the tail terminal ($β_r=r/R$ where r is the spool radius and R is the rotor radius). The HSCCC system is equipped with a Lab-Alliance Series III digital single-piston solvent pump, a Shimadzu SPD-10A UV-vis detector with preparative flow cell, a Cole-Parmer modular paperless recorder, and a ISCO Lab Alliance Foxy Jr. fraction collector.

General Procedure: Analytical TLC is performed at room temperature on Alugram pre-coated 0.20 mm thick silica gel G/UV$_{254}$ aluminum plates (20×20 cm; Macherey-Nagel, Germany). Plates are cut to 9.5 cm×20 cm before spotting. Plates are dipped in the general-purpose reagent p-anisaldehyde/sulfuric acid/acetic acid 1:1:48, drained and heated on a Camag TLC Plate Heater III at 95° C. for about 5 minutes. All TLC chromatograms are scanned for digital preservation with a Canon CanoScan scanner.

Chemicals and Abbreviations: All solvents are HPLC grade from Fisher Scientific or Sigma-Aldrich. Chemicals are purchased from the Sigma Aldrich Fluka group (St. Louis, Mo. and Milwaukee, Wis.).

The following abbreviations are used for GUESSmix compounds: r=new coccine red dye, C=caffeine, F=ferulic acid, U=umbelliferone, V=vanillin, Q=quercetin, M=coumarin, N=naringenin, Z=salicylic acid, E=β-estradiol, O=carvone, b=β-carotene. See FIG. 2 for the molecular structures.

CCC Procedures: GUESSmix samples are prepared as previously described in the form of a stock solution with a final concentration of approximately 0.1 g/mL of combined compounds.[10] The stock solution is stored at −30° C. and warmed to room temperature before use. In order to prepare the GUESSmix for a chromatographic run, 2.2 mL of the stock solution is dried under forced air. For HSCCC injection, the resulting residue is suspended in equal volumes of upper and lower phases of the appropriate solvent system. The biphasic mixture of GUESSmix compounds is then filtered and loaded into a 2 mL sample loop.

All solvent systems are thoroughly mixed, vented and allowed to separate into two distinct phases before use. The (lipophilic) stationary phase is initially pumped into the column with no rotation. Then the coils are rotated 1200 rpm as the (hydrophilic) mobile phase is pumped at a flow rate of 1 mL/min in a head-to-tail direction. In order to observe the stationary phase volume ratio in the column, the resulting effluent is collected in a graduated cylinder. When the volumes of the two phases of the eluant are approximately equal, the hydrodynamic equilibrium is apparently established. To begin the run, the standard compound mixture is injected on the column. A UV-vis detector monitored the eluant and all fractions were collected at 3 min/tube. After 254.5 mL of aqueous mobile phase is eluted from the column, organic phase is pumped into the column in the same direction, without stopping rotation. The run is stopped after lipophilic marker compound, β-carotene, eluted from the column. The UV-vis data is collected on a digital chart recorder and plotted on an Excel spreadsheet before printing. The collected fractions are reduced in volume and TLC performed to corroborate the UV-vis data.

Figure 2:
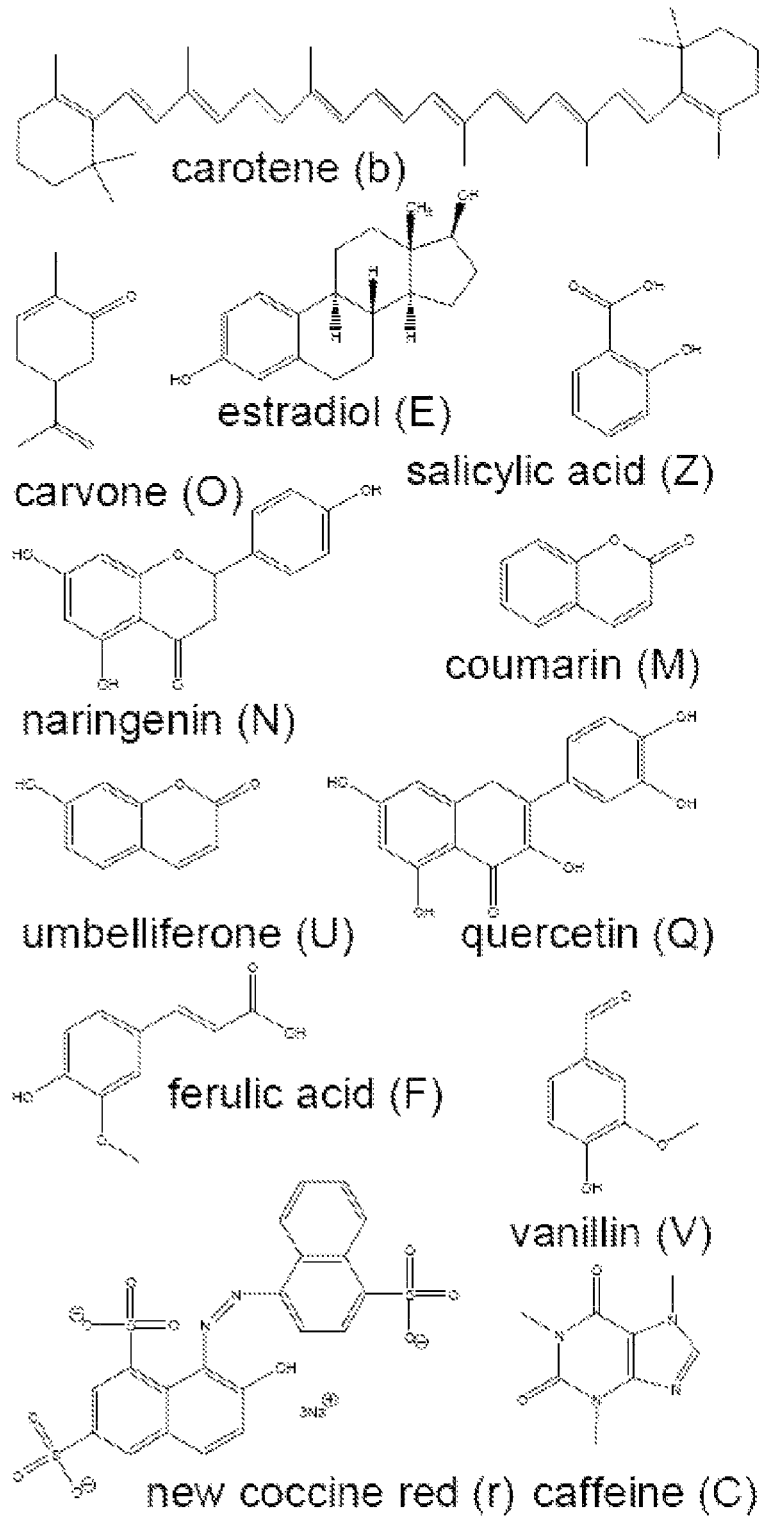
FIG. 2. The reference standards used in this example: chemical structures, names, and one-letter abbreviations FIG. 3 HSCCC separation of selected GUESSmix compounds in hexane/ethyl acetate/methanol/water 4:6:4:6. The column exhibited 58% retention of stationary phase. Elution-extrusion was begun at 254.5 mL. A is a dual-axis plot, with the K-value plotted on a secondary axis from 0 to 100 (see smooth curved solid line) and the absorbance spectrum corresponding to the lines having peaks for two different wavelengths at 230 and 280 nm. B is a plot of a portion of the K range, from 0 to 5. C is a logarithmic plot of K, centered at K=1. D is a reciprocal K plot (ReS).

RESULTS AND DISCUSSION: Thus far, CCC chromatograms are routinely documented with retention volume on the x-axis as shown in FIG. 1. This chromatogram is produced using a standard mixture previously developed to provide a TLC-based method for the Generally Useful Estimation of Solvent Systems in CCC (GUESSmix).[10] The compounds are chosen for their range of polarity, variety of functional groups and structural diversity. Their chemical structures, names, and one-letter abbreviations used throughout this study are shown in FIG. 2.

Due to practical limitations of existing CCC instrumentation, the retention volume usually cannot be measured directly, but is typically calculated by multiplying flow rate and retention time. Similar to solid support chromatography, the retention time of a particular analyte will vary according to deviations of various experimental parameters such as the flow rate, the column size, and the void volume, which in CCC is related to the stationary phase volume ratio ($S_F=V_S/V_C$). Consequently, the achievement of reproducibility of retention times greatly depends on the run-to-run reproducibility of liquid flow and volumetric control, which are rather limited in current experimental implementations. However, unlike in solid support chromatography, the K-value in CCC is constant for a particular analyte in a particular biphasic solvent system, regardless of other common experimental parameters such as flow rate, column volume, and stationary phase volume ratio. In fact, the K-value can be predicted for a particular analyte in a particular biphasic solvent system simply by distributing the compound between two liquid phases in a vial and measuring the relative concentration of the analyte in each phase. It is, therefore, highly desirable in CCC to be able to represent the elution of analytes in terms of K-value rather than volume.

Figure 3A:
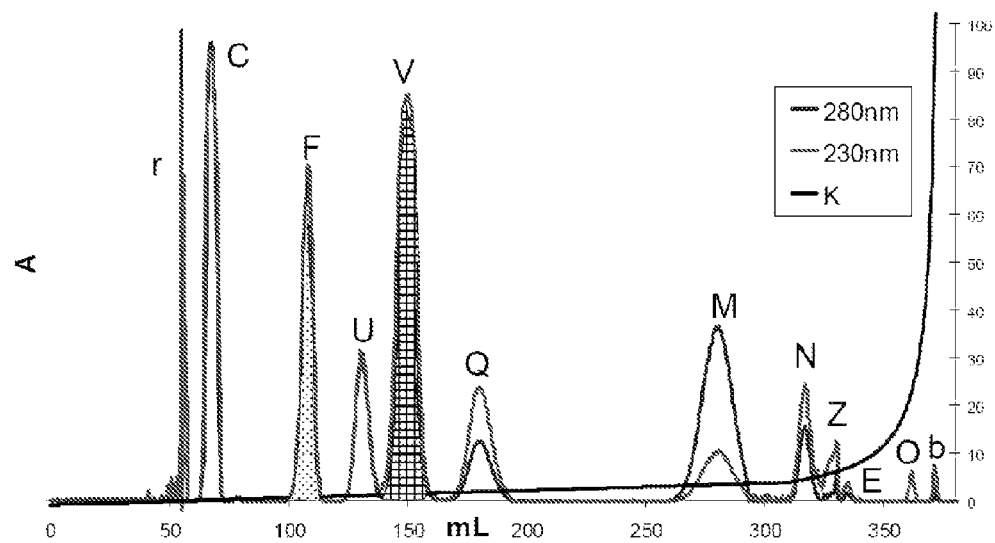

Coverage of Infinity. Since K has a scale of zero to infinity, it is a challenge to represent the whole range of K-values along the x-axis. A retention volume-based CCC chromatogram (FIG. 3A), with K on a secondary axis, or as often found as notes for individual peaks, gives some indication of the value of K as the retention volume increases.[11] While this visually establishes the principle relationship between K-values and retention volume, it is difficult to determine the K-value of any particular analyte from such dual axis plots.

Figure 3B:
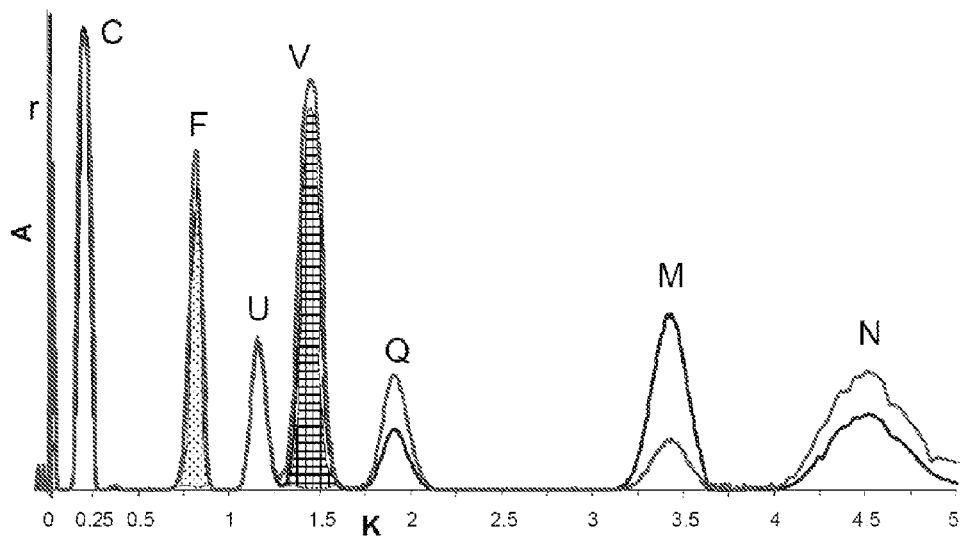

While it is possible to use K as the x-axis for narrow ranges of K, such as from 0 to 5 (see FIG. 3B), any plot that represents a limited range of K-values suffers from pronounced peak broadening as K-values increase[12], as seen in FIG. 3B for a K spanning only 0 to 5. While this ultimately results from the nature of Equation 1, and the relative large volume required for peak elution,[5] the relatively broad peak appearance does not necessarily represent poor resolution.

Figure 3C:
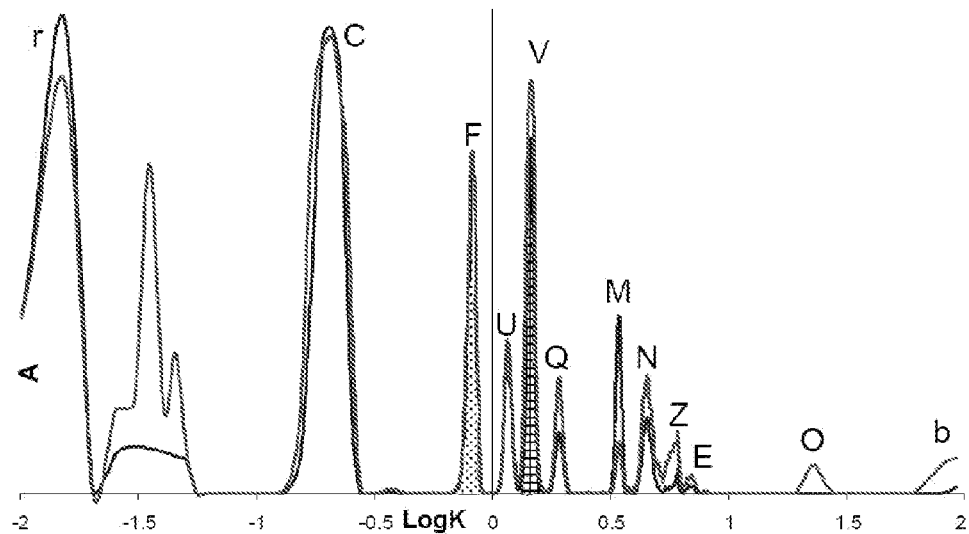

In order to address the peak broadening of late eluting analytes, a logarithmic scale representation of K-values may be used, since the logarithmic scale allows for a compression of K-values as shown in FIG. 3C.[10] The logarithmic scale, however, is not practical for comprehensive chromatograms covering the whole polarity range from K zero to infinity, because the Log K-values at K=zero and K=infinity are both infinity.

Reciprocal Symmetry (ReS) Plots. The challenge of representing the complete range of K-values (0-∞) on a single plot is addressed by dividing the plot into two regions. The x-axis values before the symmetry midline ($M_s$) correspond to the experimental x=K, whereas the x-axis values following the symmetry midline are a function of 1/K such that:

$$x = 2M_s - 1/K \qquad (4)$$

Figure 3D:
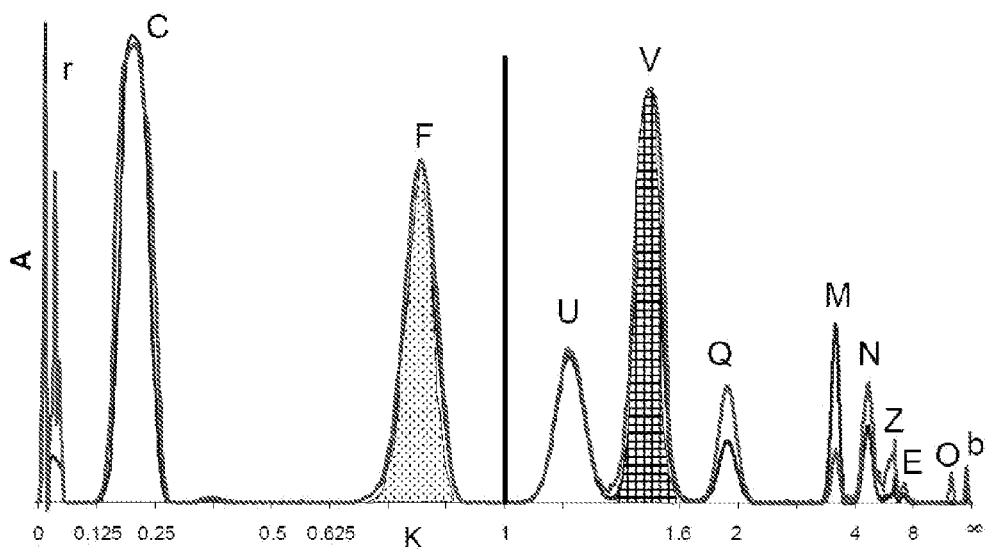

If $M_s$ is set at one, the conditions are fulfilled by plotting x=2−(1/K) for all K-values greater than one (FIG. 3D). The resulting plot is fully balanced, i.e., symmetrical, such that every value of K to the left of the $M_s$, and its reciprocal to the right of the midline, are equidistant from the symmetry midline. This establishes the Reciprocal Symmetry (ReS) plots in CCC.

The Invertible Nature of CCC. In addition to representing all K-values on one plot in a symmetric fashion as ReS plots, reciprocal plotting has the advantage of clearly exhibiting the invertible nature CCC. In CCC, the mobile and stationary phases can be reversed for any biphasic solvent system. Therefore, the analytes can be eluted from lipophilic to hydrophilic (normal phase), or from hydrophilic to lipophilic (reverse phase), depending on the choice of mobile phase. Since K is calculated by dividing the concentration of the analyte in the stationary by its concentration in the mobile phase, reversing the mobile and stationary phases in CCC will invert K-values for a particular substance in a particular biphasic solvent system. For example, a compound eluting with a K-value of 0.25 with the hydrophilic phase stationary would be expected to elute with a K-value of 4, if the hydrophilic phase was mobile. In practice, experimental conditions, such as the extra-column volume of tubing[13] and the indirect measure of volume, yield experimental results that are somewhat different than theoretical calculations.

The aforementioned reciprocal relationship emphasizes the importance of K=1 as position of symmetry ($M_s$) in CCC: A compound with K=1 will elute at the same K-value no matter which phase is chosen as the mobile phase. In addition, at K=1, Equation (1) becomes:

$$V_R = V_M + V_S = V_C \qquad (5)$$

In other words, an analyte with K=1 will always elute at one column volume irrespective of the stationary phase volume ratio ($S_F$). Therefore, if the CCC chromatography of the GUESSmix standard (ReS plot in FIG. 3D) is performed in the same solvent system, but with the hydrophilic phase as the stationary phase, not only would the order of elution be reversed, but also the resulting ReS plot is an exact inverse (mirror image) of the chromatogram in FIG. 3D.

Relationship Between Sweet Spot and Symmetry Axis. Another advantage of the ReS plots is that they can be centered in such a way so as to draw attention to the "sweet spot" of the CCC chromatogram.[10] The sweet spot concept refers to the interval of K-values that represent a window of optimal resolution of analytes in CCC. In the absence of elution-extrusion ("classical" mode), the K-value interval of the sweet spot may be delimited as 0.25<K<4.[10] However, the elution-extrusion technique effectively extends the sweet spot interval towards analytes with higher K-values. While elution-extrusion may be initiated at any point during the run, the choice of when to begin extrusion is a balancing act. In general, the longer the time before beginning elution-extrusion, the wider K-value interval will be included in the sweet spot. On the other hand, waiting too long to begin extrusion tends to produce excessive sample band broadening and long run times.[6] The ReS plot symmetry midline, $M_s$, can be adjusted to highlight the sweet spot K-values of interest by introducing a multiplication factor (m) such that $$M_s - K = f(m/K) - M_s \qquad (6)$$

Figure 4:
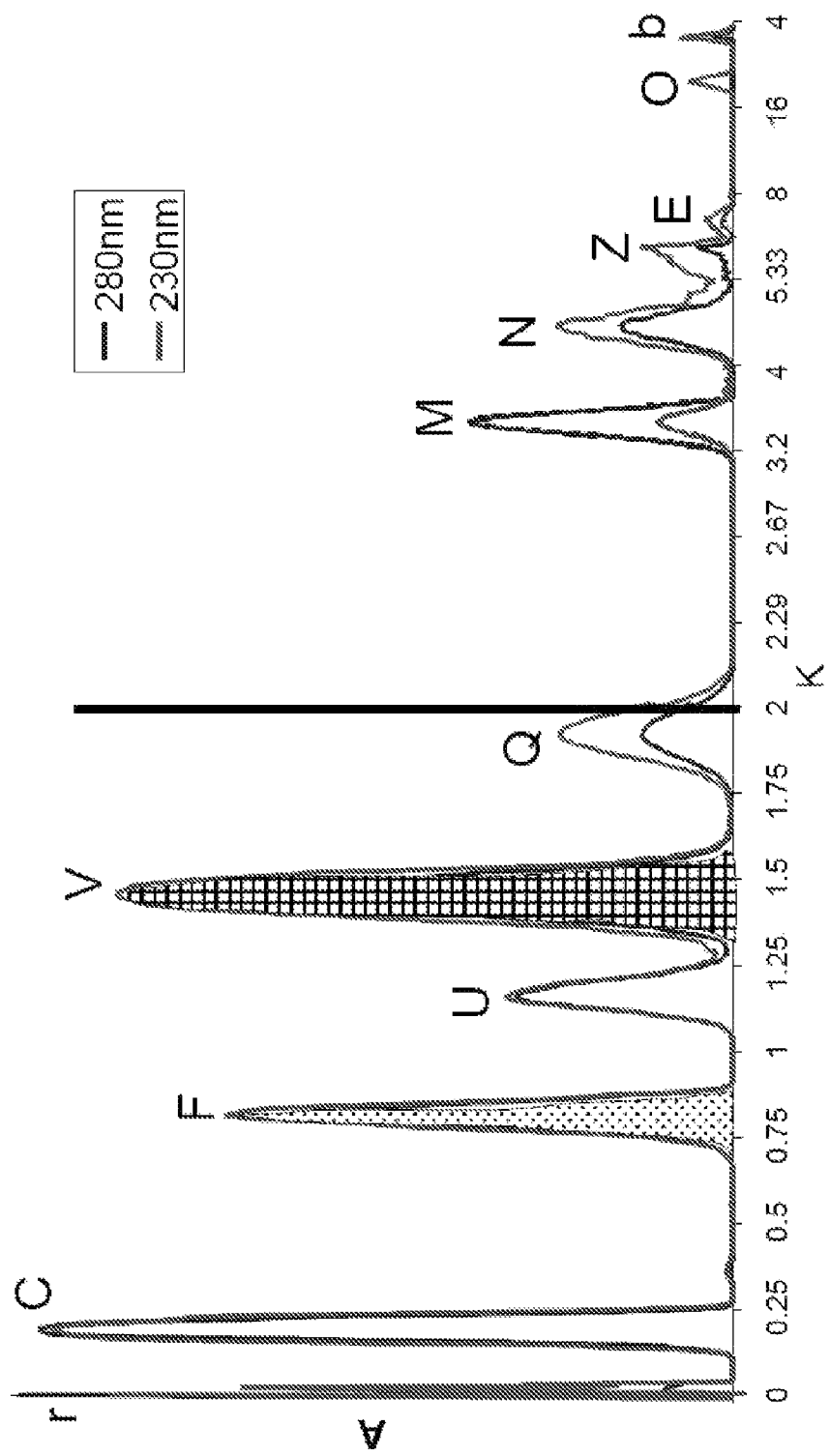
FIG. 4 HSCCC separation of selected GUESSmix compounds in hexane/ethyl acetate/methanol/water 4:6:4:6 and resultant ReSS plot, centered at K=2. The column exhibited 58% retention of stationary phase. Elution-extrusion was begun at 254.5 mL. K=0.25 at 67.5 mL and K=16 at 359 mL.

In the case where the K of a compound coincides with the $M_s$, K=$M_s$, the value for m=$M_s^2$. Therefore, the chromatogram can be plotted with x=$2M_s - (M_s^2/K)$ for all K-values greater than $M_s$. In the given GUESSmix experiment, the sweet spot extends from K=0.25 to K=16 and it will be centered on the symmetry midline in a $M_s$=2 chromatogram. Shifting the $M_s$ midline according to the sweet spot characteristic of a given combination of instrumentation and solvent system, a Reciprocal Shifted Symmetry (ReSS) plot is obtained (FIG. 4).

A ReS plot, with K and 1/K positioned on either side of the symmetry midline, $M_s$=1, is an improved system for representing CCC chromatograms. All K-values, from zero to infinity, can be comprehensively placed on the x-axis. The reciprocal plot also demonstrates the invertible nature of CCC that is a result of the ability to exchange the mobile and stationary phases used for elution. The midline of the reciprocal plot may be adjusted in ReSS plots order to show clearly K-values in the high resolution portion of the chromatogram. Improved representation of peak shape across the whole polarity range of a given CCC chromatogram is an added advantage of ReSS plots. Finally, although the ReS and ReSS experiments provided herein are developed using high-speed CCC (HSCCC) instrumentation based on the J-type centrifuge, the concept is transferable to centrifugal partition chromatography (CPC), among others.

In retention volume chromatograms (FIG. 1), peak shape of compounds eluting after K=1 tend to be elongated and distorted, especially when compared with GC or HPLC chromatograms. This is eliminated in ReSS CCC plots (FIG. 4) which are centered on the sweet spot of optimal resolution minimize peak widths. Thus, ReSS plots more adequately reflect the high resolution of CCC. In this way, both reciprocal plots, ReS and ReSS, will provide reproducible representations of peak width and resolution. This applies regardless of the timescale of the chromatogram (short vs. long analysis time), although it should be noted that resolution improves as the retention volume increases, which means that there can be an advantage to longer run times. Considering both the improved representation of peak shape and the aforementioned uniformity of the approach, ReS and ReSS plots provide a solid basis for cross-platform comparison of CCC chromatograms and instruments.

Head/tail center/periphery designations: An individual coil of a multi-layer coil instrument is typically wound with the tubing entering on one side of the coil and exiting on the other. The coil, therefore, has two sides: the "center" side is where the tubing enters and is initially wrapped around the base of the bobbin, and the "periphery" side is the where the tubing exits after wrapping has finished. The direction of liquid flow through the coil can be center-to-periphery or periphery-to-center.

In high-speed counter-current chromatography (HSCCC), the coil is rotated at high speeds about its axis. The direction of rotation relative to the direction of coil winding determines the position of the coil head and tail. The head is defined as the outlet that the liquid will flow through spontaneously under the influence of the Archimedean screw force generated by the rotation.

There are, in consequence, four different possibilities for winding and rotation: 1) head (center) to tail (periphery); 2) head (periphery) to tail (center); 3) tail (center) to head (periphery); 4) tail (periphery) to head (center).

In conclusion, it is not sufficient to simply state that the direction of flow in a HSCCC column is head-to-tail or tail-to-head. The position of the head at the center or periphery of the coil must also be specified in order to accurately describe the experimental parameters. The direction of flow, as well as the position of the head on the coil, has consequences for instrument performance, particularly the stationary phase volume ratio ($S_F$).

EXAMPLE 2

Performance Characteristics of Countercurrent Separation in Analysis of Natural Products of Agricultural Significance A standard test mix consisting of 21 commercially available natural products of agricultural significance, termed the GUESSmix, was employed to measure the countercurrent chromatography performance characteristics of a very popular quaternary solvent system family made up of hexane-ethylacetate-methanol-water (HEMWat). The polarity range of the GUESSmix combined with the elution-extrusion countercurrent chromatography (EECCC) technique and the reciprocal symmetry (ReS) and reciprocal shifted symmetry (ReSS) plots (outlined in Example 1) allow liquid-liquid distribution ratios ($K_D$) to be plotted for every compound eluted on a scale of zero to infinity. It was demonstrated that 16 of the 21 GUESSmix compounds are found in the optimal range of resolution ($0.25 < K_D < 16$) of at least one HEMWat solvent system. The HEMWat solvent systems represented by the ratios 4:6:5:5, 4:6:4:6, and 3:7:4:6 posses the most densely populated optimal ranges of resolution for this standard mix. ReS plots have been shown to reveal the symmetrical reversibility of the EECCC method in reference to $K_D=1$. This study lays the groundwork for evaluation and comparison of solvent system families proposed in the literature, as well as the creation of new solvent system families with desired performance characteristics.

The chemical analysis of food demands a wide range of chromatography methods to separate and characterize individual natural products, which are contained in complex mixtures and are embedded in complicated matrices. Because of its ability to achieve high-resolution separations, countercurrent chromatography has been shown to play a significant role in the analysis of food products. In particular, the analysis of secondary natural products of health interest contained in functional foods has been demonstrated, among others, by the work with cranberry phytochemicals (1), glucoraphanin from broccoli (2), tea catechins (3,4), various components of wine (5-10), soy isoflavones (11), anthocyanins from fruits (12-15), and antioxidants (16,17). Moreover, countercurrent methodologies have played a role in the identification and removal of contaminants and toxins in food in the cases of deoxynivalenol from moldy corn and rice (18), olitrem B from endophyte-infected ryegrass (19), staphylococcal enterotoxin A from milk (20,21), and GGPL-I & GGPL-III from *Mycoplasma fermentans* (22). Further research topics in which countercurrent separations have been useful are the analysis of pigments, flavors, and aromas from various plant sources (9,17,23-25).

Countercurrent separation (CS) is a powerful liquid-based method for the isolation of food ingredients and phytochemicals in general. CS technology has been implemented at any level of sample load from analytical to process-scale, and is often referred to as [high-speed] countercurrent chromatography ([HS]CCC) and [centrifugal] partition chromatography ([C]PC). There are several advantages of this type of separation: extensive preparation of a solvent, supercritical fluid or essential oil extract is not necessary; all compounds introduced to the column are recovered; the structural integrity of components is preserved in a liquid-liquid environment; maximum surface area interaction between the two phases allows for optimal use of both phases; and, once an appropriate solvent system is selected, separation scale-up is straightforward, because the liquid-liquid distribution ratio ($K_D$) is independent of column volume, flow rate, stationary phase retention, and the length of the chromatographic run. The distribution ratio is defined as the concentration of a particular compound in the stationary phase divided by the concentration of the compound in the mobile phase. Representing a key parameter in countercurrent analysis, knowledge of the $K_D$ of analytes is key to the design of CS methods, and allows the arithmetic prediction of the separation based on instrument parameters (26).

The choice of the two-phase solvent system is the most critical and often the most time-consuming aspect of CS. Compared to the far more popular solid-support chromatography, the selection of CS solvent systems is equivalent to concurrently choosing both column and eluant. Solvent system choice can be divided into two operations: the choice of a solvent system family; and the selection of component solvent proportions. A solvent system family is created by combining two or more solvents that form a biphasic system when mixed. The relative proportions of the constituent solvents within a family can be modified almost endlessly, therefore, organized systems of solvent system family members have been developed in the CS literature (27-30). Biphasic solvent systems composed of varying concentrations of hexane-ethyl acetate-methanol-water are used extensively to separate and isolate phytochemicals from extracts (31-40). The HEMWat family of seventeen hexane-ethyl acetate-methanol-water solvent systems has been constructed with a progression of polarity from most polar (+8) to least polar (−8), as shown in Table 1. A solvent system family organizes the potentially unlimited number of combinations into a manageable, yet representational series of solvent systems.

A recent innovation in CS methodology allows the continuous elution of all the analytes in a mixture in one chromatographic run without the need for a solvent gradient (41). The elution extrusion method (EECCC) employs the fact that the stationary liquid "column" used in the first two phases of elution may be eluted in its entirety during the last phase of the chromatographic run. As a result, analyte resolution is retained and the $K_D$ may be calculated for each compound based on its elution volume. Until now, countercurrent chromatograms have been plotted with time or volume on the x axis. This practice makes it impossible to represent the relative and absolute $K_D$ values corresponding to each eluted peak. Reciprocal symmetry (ReS) and reciprocal shifted symmetry (ReSS) plots have been recently proposed to allow $K_D$ to be plotted for every compound eluted in EECCC on a scale of zero to infinity (42). ReS plots clearly demonstrate that the value of $K_D$ for each analyte in a given solvent system is independent of the length of a chromatographic run (41). Another application of ReS/ReSS plots is the direct visual comparison of changes in $K_D$ for the same mixture of analytes separated in different solvent systems (43). Since $K_D$ is independent of column volume, ReS/ReSS plots may also be used to compare performances of different countercurrent instruments by separating the same mixture of compounds in the same solvent system on instruments of various column volumes.

Building a bridge between complex natural samples, such as foods and agricultural products, and theoretical models of CS, a mixture of natural products that represents the diverse polarities, structural characteristics, and functional groups found in natural product extracts has been developed as a means of modeling the behavior of analytes by CS (FIG. 5) (44). Experiments with this mixture have clearly shown the value and necessity of optimizing chromatographic conditions in order that the analytes of interest occupy a region of optimal resolution determined by their $K_D$ values. Combined with ReSS plots, this mixture of natural products has very recently been shown to also be a powerful tool in evaluating solvent systems and solvent system families (43).

Evaluating solvent systems continues to be a major challenge of CS. Not only is there a wide choice of solvent system families with a particular combination of solvents (e.g. hexane-ethyl acetate-methanol-water), but the relative volumes of the solvent components can be varied in an infinite manner. There is, therefore, a great need for methodologies by which to evaluate and predict solvent system behavior for a variety of analytes to determine the selection of both composition and volume ratio of solvents so they can successfully be used in a separation procedure. Thus, methodology by which solvent system performance can be measured is in demand as it is crucial for the systematic exploration of the varied chemical constituents of foods and agricultural products.

Instrumentation. High-speed countercurrent chromatography (HSCCC) was performed on a Model CCC-1000 J-type instrument (Pharma-Tech Research Corporation, Baltimore, Md., USA). It consisted of a self-balancing three-coil centrifuge rotor and coils wrapped with 1.6 mm internal diameter of PTFE (Teflon) tubing to a volume of 40 mL each. The distance between the coil holder axis and central axis of the centrifuge (R) was 7.5 cm. The β ratio ($β_r$) varied from 0.73 at the head to 0.47 at the tail ($β_r=r/R$ where r is the spool radius and R is the rotor radius). The rotation of the coil assembly relative to the coil winding situated the head at the periphery position. Furthermore, the HSCCC system included a Lab-Alliance Series III digital single-piston solvent pump, a Shimadzu SPD-10A UV/Vis detector with preparative flow cell, and a fraction collector. Chromatogram data was collected with a Cole-Parmer 80807-00 modular paperless recorder and transferred in digital form to an Excel spreadsheet.

Thin Layer Chromatography. Collected fractions were reduced in volume and analyzed with TLC at room temperature. Alugram 20×20 cm pre-coated 0.20 mm thick silica gel G/UV$_{254}$ aluminum plates (Macherey-Nagel, Germany) were cut to 9.5 cm×20 cm before spotting. Plates were dipped in the general-purpose reagent (4% p-anisaldehyde, 4% sulfuric acid, 92% acetic acid), drained, and heated on a Camag TLC Plate Heater III at 95° C. for about 5 min. Digital preservation of all TLC chromatograms was achieved with a Canon CanoScan LiDE20 scanner.

Chemicals. HPLC grade solvents were purchased from Fisher Scientific or Sigma-Aldrich. GUESSmix component chemicals were purchased from the Sigma Aldrich Fluka group (St. Louis, Mo. and Milwaukee, Wis.). FIG. 5 lists the twenty one GUESSmix compounds employed in this study. The biphasic liquid system selected is the mixture of hexane-ethyl acetate-methanol-water in various volume ratios as defined in Table 1. The stationary phase was the lighter organic phase and the mobile phase was the denser aqueous phase.

HSCCC Procedures. Samples of GUESSmix compounds were prepared as previously described in the form of a stock solution with a final concentration of approximately 0.1 g/mL of combined compounds. The stock solution was stored at −30° C. and warmed to room temperature before use. The GUESSmix compounds were prepared for a chromatography by drying 2.2 mL of the stock solution under forced air, and the resulting residue was then suspended in equal volumes of upper and lower phase of the solvent system. The biphasic mixture of GUESSmix compounds was then filtered and loaded into a 2 mL sample loop.

The solvent system was thoroughly mixed, vented and allowed to separate into two distinct phases before use. The lipophilic lighter stationary phase was initially pumped into the column with no rotation. Then the coils were rotated at 1200 rpm as the hydrophilic denser mobile phase was pumped at a flow rate of 1 mL/min entering the column head. In order to observe the volume of stationary phase eluted from the column, the resulting effluent was collected in a graduated cylinder. The hydrodynamic equilibrium was considered to be established when the volumes of the two phases of the eluant were approximately equal. The standard compound mixture was injected on the column, the fraction collector started, and the recorder turned on. All fractions were collected at 3 min/tube. After a predetermined volume ($V_{CM}$, also called the switch volume) of aqueous mobile phase had eluted from the column, the organic phase was pumped into the column, marking the beginning of sweep elution and subsequent extrusion, and also entering through the column head. After the lipophilic marker, β-carotene, eluted from the column (120 mL after $V_{CM}$) the run was discontinued. The collected fractions were reduced in volume and TLC performed to corroborate the UV/Vis data.

Correlating Shake Flask Partition Coefficients with CS Distribution Ratios. One of the best-known ways to determine the polarity of molecule is to measure or calculate the partition coefficient of the molecule in a biphasic mixture of octanol and water ($K_{octanol/water}$) (45). The partition coefficient is the concentration of an analyte in the upper phase divided by the concentration of the same analyte in the lower phase of an equilibrated biphasic solvent system. The partition coefficient of an analyte in any biphasic mixture is related to the liquid-liquid distribution ratio, $K_D$, of the same analyte in a countercurrent separation experiment as calculated by $K_D=(V_R-V_M)/V_S$ (26). In practice, the retention volume of the analyte ($V_R$) is calculated from the retention time and flow rate. The mobile phase volume ($V_M$) and stationary phase volume ($V_S$) are observed for each chromatographic experiment. According to countercurrent separation theory, K and $K_D$ are equivalent provided that four conditions are met. First, it is assumed that both processes have reached equilibrium. The shake-flask experiment represents a static equilibrium whereas the countercurrent process is a dynamic equilibrium. Second, a one-to-one volume ratio in the shake flask experiment corresponds to the dynamic equilibrium conditions of the countercurrent process. Third, the upper phase is the stationary phase for the CS experiment. If the lower phase is the stationary phase, then $1/K \equiv K_D$, since the $K_D$ in CS theory is defined as the concentration of an analyte in the stationary phase divided by its concentration in the mobile phase. Fourth, the compound is present in the same chemical form in each process. Ionization and solute-solute interactions such as dimerization of carboxylic acids, would change the chemical form of an analyte in solution. Indeed, despite the exigencies of these conditions, CCC has been used to determine $K_{octanol/water}$ of compounds in certain cases (46-49).

There are at least three practical considerations that come into play, however, when comparing shake flask K-values with $K_D$ values calculated from a CS run. Firstly, it must be kept in mind that the two values are measured by different means. Shake flask K-values are typically determined by UV absorption ratios either directly or after HPLC separation. On the other hand, the value of $K_D$ is determined by selecting a peak position for the retention time of the analyte in order to determine the retention volume, $V_R$, of the analyte. Secondly, the influence of other compounds present in the mixture may be significant. Shake flask partition coefficients were determined with a single compound in a biphasic system in this study. By contrast, distribution ratios were determined as part of the GUESSmix separated over the course of a CS experiment. Thirdly, proximity to one is a factor for both methods. Experimental calculations of both K and $K_D$ above 10 and below 0.1 lose some precision since the measurements for numerator and denominator differ by a factor of ten or more.

Figure 6C:
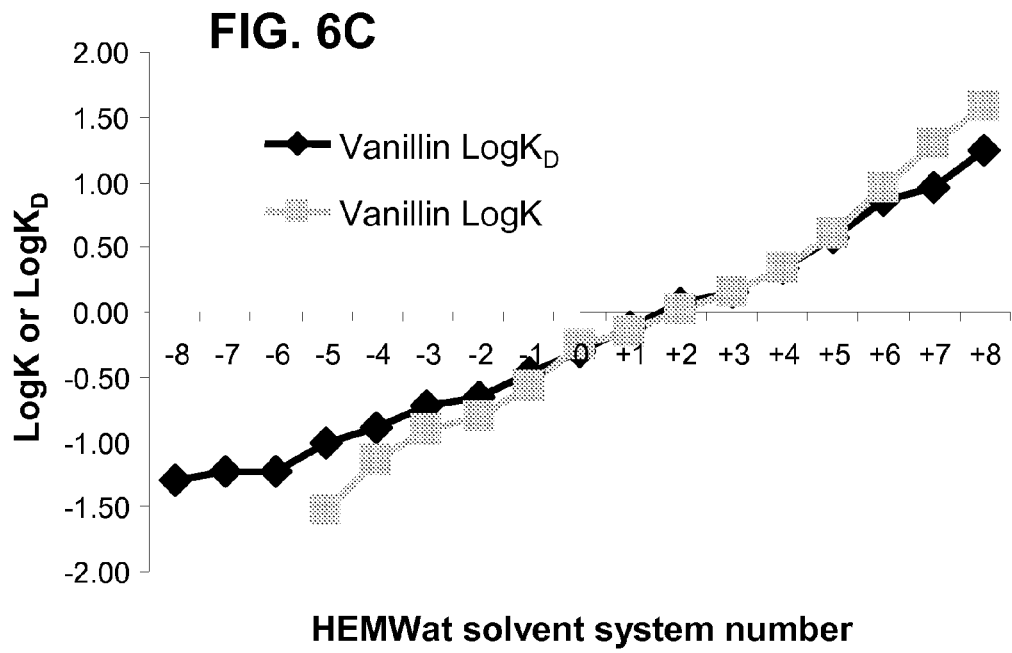
FIG. 6 Comparison of shake flask partition coefficients (K) and liquid-liquid distribution ratios ($K_D$) for three of the GUESSmix compounds in various HEMWat solvent systems (see TABLE 1), A. coumarin (M); B. umbelliferone (U); C. vanillin (V); D is a histogram that shows the frequency of Δ Log $K_D$ or Δ Log K-values for 14 GUESSmix compounds.

In FIGS. 6A-C, shake-flask partition coefficients are compared with liquid-liquid distribution ratios for three different analytes. As expected, the correlation for K and $K_D$ is closest for values between 10 (Log 10=1) and 0.1 (Log 0.1=-1). Overall, the correlations are quite close considering the theoretical conditions for equivalence and practical experimental considerations described in the preceding paragraphs.

Figure 6D:
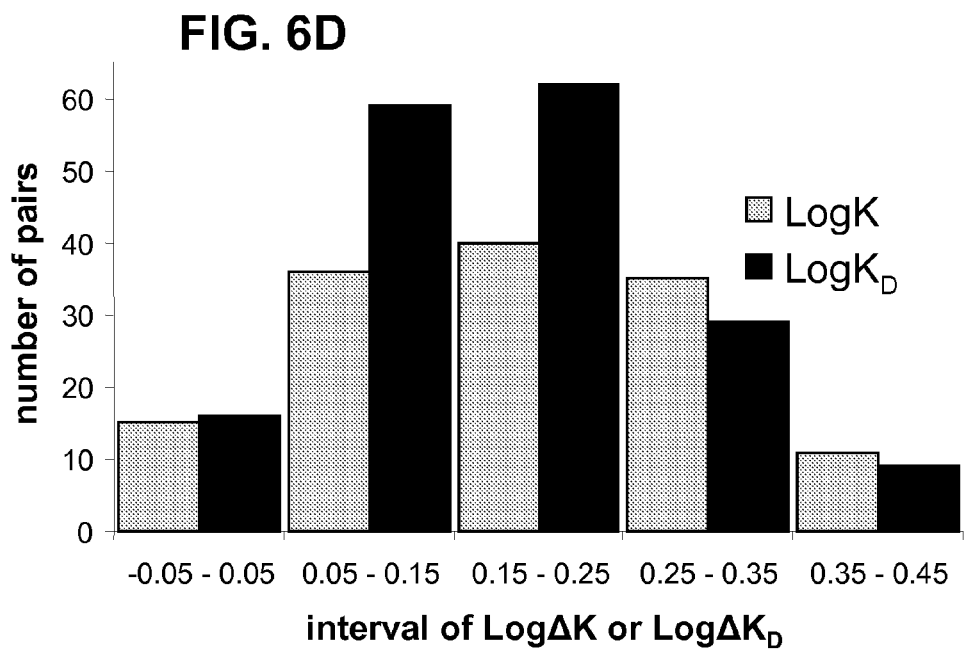

Linear Behavior of Both Log K and Log $K_D$ Plots. The linearity of the resultant Log K/Log $K_D$ plots in FIGS. 6A-C were not an expected outcome of this study. The solvent combinations selected to make up the HEMWat family do not necessarily indicate that the Log $K_D$ plots will be linear. As seen from FIG. 6D, the majority of the slopes of the Log $K_D$ plots fall in a narrow range. This provides a way to predict the $K_D$ of an analyte in any HEMWat solvent system given its $K_D$ in one HEMWat solvent system by employing the average slope of Log $K_D$=0.16.

Solvent System Family Mapping. The shaded area of TABLE 2 corresponds to the region of optimal resolution for this particular series of solvent systems. The region of optimal resolution between $0.25<K_D \leq 16$ was chosen by consideration of literature reports of optimal separation (26,27) as well as the chromatograms generated by this particular series of experiments. At this point, there is no established interval, or formula for deriving the interval, corresponding to the region of optimal resolution. However, the traditional understanding of the region of optimal separation as centered around $K_D=1$ has been modified due to the EECCC method, which has the effect of extending the region of optimal resolution to $K_D$ values represented by retention volumes greater than one column volume (50).

The HEMWat family of solvent systems has the capacity to separate a varied range of phytochemicals as exemplified by the observation that 16 of the 21 representative compounds are found in the region of optimal resolution in at least one HEMWat solvent system. In fact, compounds occupying the designated region of optimal resolution represent 115 out of 357 data entries in TABLE 2. The polarity range of those GUESSmix compounds found in the region of optimal resolution possess Log $K_{octanol/water}$ values from -1.88 (chlorogenic acid) to 9.52 (cholesterol). The GUESSmix compounds themselves represent a wide range of polarities most of which have Log $K_{octanol/water}$ values that suggest good absorption and permeability drug characteristics. Certainly, there is an interest in separating compounds which exhibit polarities outside of this range, nevertheless, the HEMWat solvent system family cuts a wide swath through the range compound polarities that are likely to be of interest to the agricultural chemist.

When compared to previously evaluated solvent system families, such as chloroform-methanol-water, ethyl acetate-butanol-water, and t-butylmethylether-acetonitrile-water, the HEMWat family has a wider continuous polarity range than other solvent system families (43,44). In other words, the HEMWat solvent system family is a good first try when targeting the separation of a compound or series of compounds that have no precedence in CS. Unless the polarity of the target compound lies outside of the fairly wide range of HEMWat-compatible values, the compound(s) will likely be separated with acceptable resolution in one or more of the HEMWat solvent systems. This proposition is affirmed by the overwhelming popularity of solvent systems composed of hexane-ethyl acetate-methanol-water, and closely related mixtures thereof, in CS. For example, in a recent review article, hexane-ethyl acetate-methanol-water solvent systems were employed in one-third of all reported (20 out of 60 reviewed) CS applications (51).

The distribution of $K_D$ values in a given solvent system is affected, certainly, by the choice of compounds for this study. The GUESSmix was conceived as an instrument to allow comparison between solvent systems and not as an absolute measure of solvent system polarity or performance. Useful information on the comparative polarity and selectivity between solvents may be gained by such an approach, particularly when the compounds in the test mix represent a range of molecular weights, functional groups, and polarities as determined by their Log $K_{octanol/water}$ values (43).

Another feature of the HEMWat solvent system comparison may be ascertained from TABLE 2. The solvent systems termed HEMWat +2, +3, and +4 have the highest population of compounds in their respective regions of optimal resolution while the populations decline steadily on both the more polar and less polar sides. *Therefore, HEMWat +3 likely represents a portal with which to enter this solvent system family.* If a compound mixture is tested with HEMWat +3, and the target compound(s) are not present in the region of optimal resolution, it is unlikely that other HEMWat solvent systems will be able to resolve these compounds—thus the portal designation of HEMWat +3. However, if a compound mixture is tested with the HEMWat +3 and the target compound(s) are present in the region of optimal resolution but not well resolved, it may be useful to try other members of the HEMWat solvent system family to better resolve these compounds.

Figure 7:
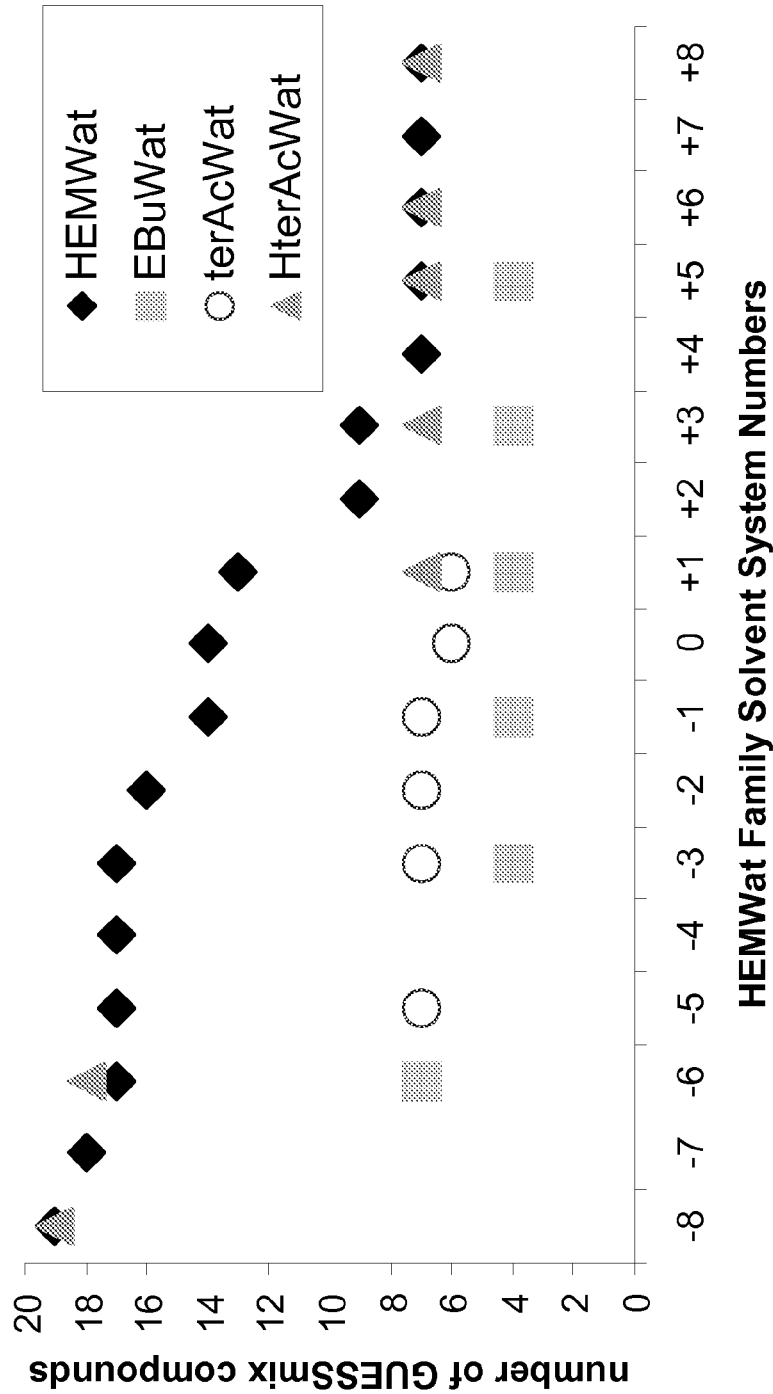
FIG. 7 Number of GUESSmix compounds (out of 21) which have $K_D$ values less than or equal to one in a variety of solvent systems. Data for ethyl acetate-n-butanol-water (EBuWat), t-butylmethylether-acetonitrile-water (terAcWat), and hexane-t-butylmethylether-acetonitrile-water (HterAcWat) is found in J. Chromatography A (2007) 1151: 51-59.

Polarity Comparison. The relative polarities of solvent systems may be compared by dividing compounds into those with $K_D \leq 1$ and those with $K_D > 1$ for a particular solvent system. In FIG. 7, the values describing the number of compounds with $K_D \leq 1$ for the HEMWat solvent system family cross the midpoint of the y axis between +1 and +2. This overlaps with the series of solvent systems with the most highly populated regions of optimal resolution. This method of measuring relative polarities may be used to compare the HEMWat solvent system family to previously published solvent systems (43). It can be seem from FIG. 7 that HEMWat covers a much larger polarity range than ethyl acetate-butanol-water (EBuWat) and t-butylmethylether-acetonitrile-water (terAcWat). The polarity range of HEMWat and hexane-t-butylmethylether-acetonitrile-water (HterAcWat) is similar, but HEMWat covers it continuously, whereas HterAcWat does not. This offers yet another explanation for the popularity of the HEMWat solvent system family.

Figure 8:
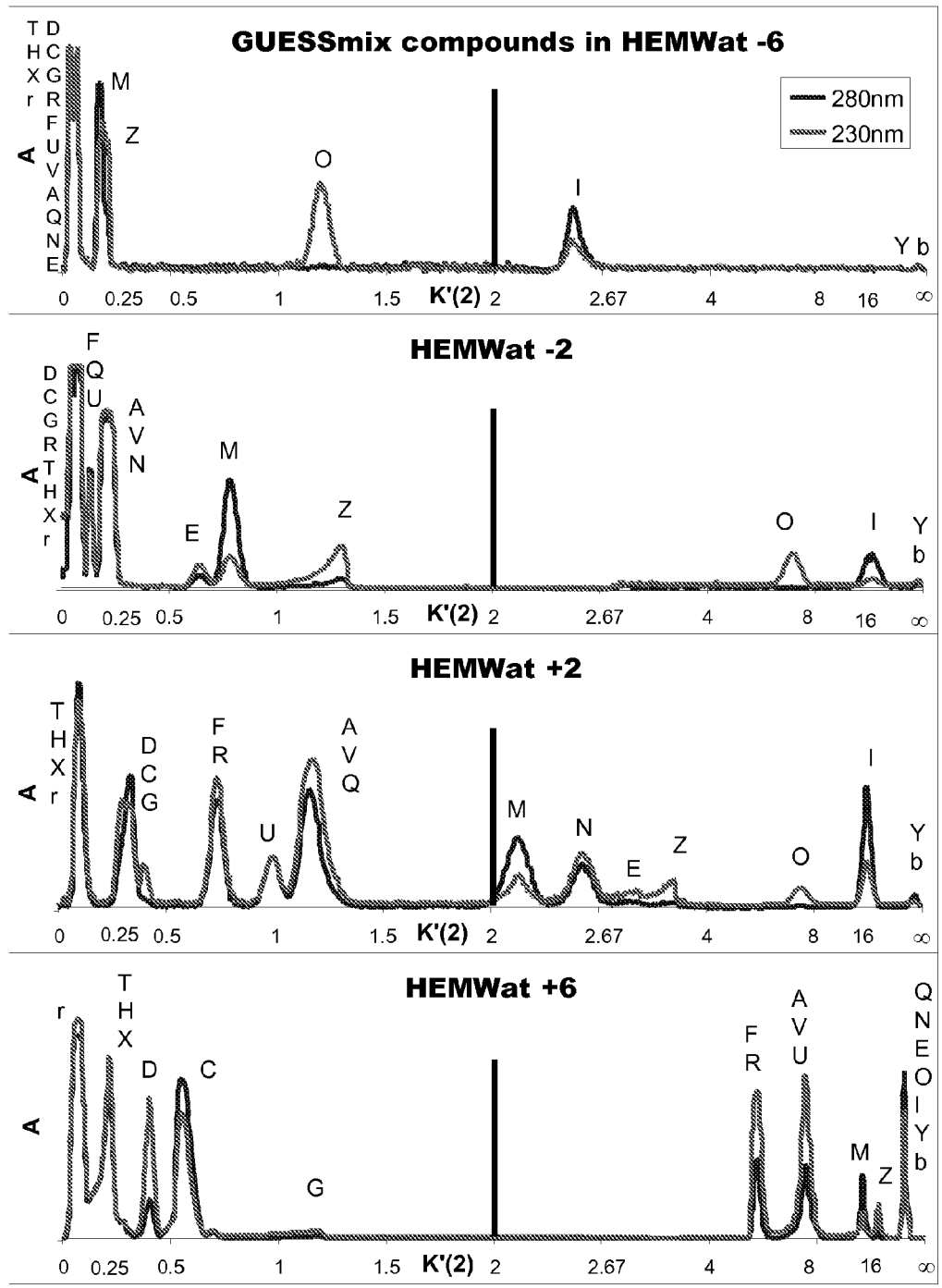
FIG. 8 ReSS plots centered at $K_D=2$ for the chromatography of the GUESSmix compounds in four HEMWat solvent systems: A HEMWat −6; B HEMWat −2; C HEMWat +2; D HEMWat +6. The individual compounds are identified by their one-letter abbreviations. These experiments facilitate analysis of "optimal" solvent systems for particular analytes of interest.

ReSS Plots. ReSS plots are particularly useful in comparing the behavior of the GUESSmix in HEMWat solvent systems. Since the x-axis of the ReSS plot is in terms of $K_D$, and not in volume, it offers a direct way to compare solvent systems with much more richness than a solvent system map. A reasonable approach to decide where to situate the midline of ReSS plot is that it should be approximately at the volumetric center of the run. The volumetric center is the point where half the volume of a chromatographic run has been eluted. If readings are taken, or fractions collected, at regular volume intervals, the volumetric center is also the center of data points. For example, the volumetric center of the HEMWat −2 experiment in FIG. 8 is at $V_R = 210$ mL which corresponds to $K_D = 2.15$. Thus, placing the midline at $K_D = 2$ is most appropriate as it balances the number of data points on each side of the x-axis and yields peak shape symmetry along the midline that is compatible with the other chromatograms.

The ReSS plot chromatograms in FIG. 8 show the chromatograms of four selected solvent systems represented in TABLE 2. ReSS plots of chromatograms reveal the high resolution capabilities of CS as well as the displacement of individual analytes to higher $K_D$ values as the polarity of the solvent system increases. The ReSS plot chromatograms also show the shape and resolution of the compound peaks that is not well represented in the solvent system map in TABLE 2. For HEMWat −6, the majority of the GUESSmix compounds are gathered in the unresolved polar region with $0 \leq K_D < 0.25$. As the HEMWat numbers increase, most of these compounds migrate across the region of optimal resolution, $0.25 \geq K_D < 16$, and end up gathered together in the unresolved non-polar region with $16 \leq K_D < \infty$ of HEMWat +6.

Figure 9:
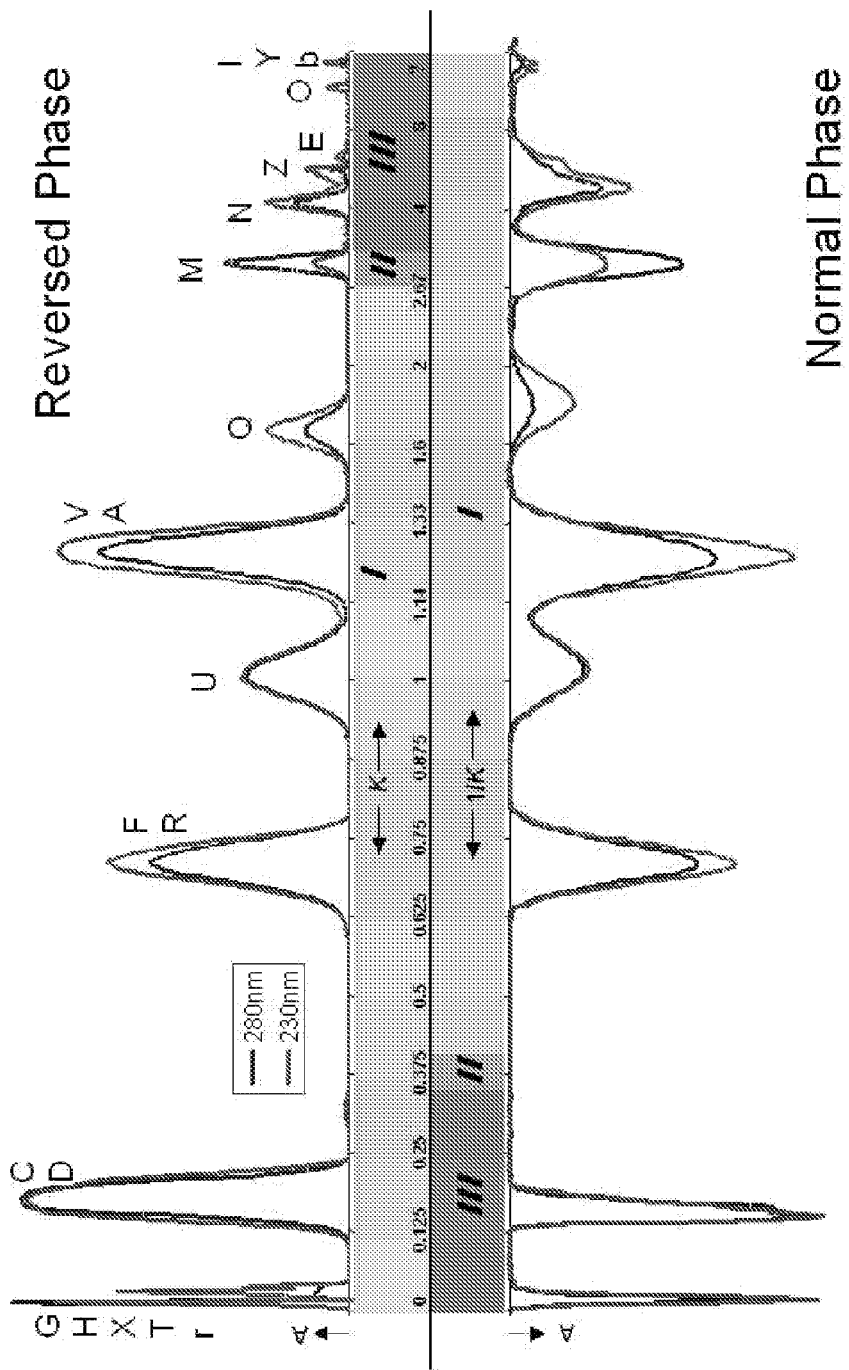
FIG. 9 ReS plots for GUESSmix in HEMWat +3 in both reversed phase and normal phase modes. The normal phase chromatogram is plotted backwards and upside down to share the same x-axis with the reversed phase plots. The Roman numerals I, II, and III represent the three stages of EECCC: classical elution, sweep elution, and extrusion, respectively.

The Symmetrical Nature of Countercurrent Separations. ReSS plots make it possible, for the first time, to experimentally demonstrate the full symmetrical reversibility of the CS method between normal phase and reversed phase modes, as shown in FIG. 9. When the lower phase is the mobile phase of the CS experiment, then $K_D = K$. However, if the upper phase is the mobile phase, then $K_D = 1/K$. Therefore, the normal phase is plotted backwards (and upside down) in FIG. 9. Generally, the extrusion peaks in step III of the EECCC run are narrower and better resolved than the peaks in classical elution, EECCC step 1. This is because peak resolution is directly proportional to the time the compound spends in the column (41).

This study establishes EECCC paired with ReSS plots and HEMWat +3 as biphasic solvent system as a portal method to develop CS methods for the separation of complex natural mixtures. Utilizing an array of $K_D$ values of the standardized GUESSmix, performance of CS separations can be predicted for unknown analytes that fall into the range of HEMWat polarities. The full symmetry of normal and reversed phase CS, the simplicity of the GUESSmix-based polarity matching, and the general advantages of CS as a liquid-liquid separation technology are added advantages. This lays the groundwork for evaluation and comparison of other solvent system families proposed in the literature, as well as for the creation of new families with desired performance characteristics.

Centrifugal Partition Chromatography (CPC). Historically, CPC refers to the hydrostatic methods of countercurrent chromatography, which uses centrifugal-force (counter-)current flow emerging from revolution around only one axis. CPC instruments use rotating seals, and generally operate at higher flow rates and higher back pressures than hydrodynamic CCC instruments.

Classical Elution. Elution of analytes with the mobile phase being pumped through the column while the stationary phase is being held in the column through, e.g., centrifugal force. See also EECCC.

Column Volume. One of the principle instrumental parameters in countercurrent separation is the total volume of the column, which is important when understanding analyte elution and when calculating countercurrent chromatograms. Total column volume ($V_C$) also determines the load capacity of a particular machine.

Countercurrent Chromatography (CCC). A continuous liquid-liquid partition separation where one liquid phase is immobilized by gravitational or centrifugal force, not by a solid support. The term "CCC" has been coined for equipment developed in the laboratory of Dr. Yoichiro Ito of NIH (Bethesda, Md.), ranging from the early droplet (DCCC) and rotation locular (RLCCC) to the centrifugal multi-layer (ML-CCC) and high-speed (HSCCC) instruments. Commercialized HSCCC instruments that are based on the coil planet centrifuge principle, lack a rotating seal, and make use of centrifugal force for both phase mixing and phase separation. Historically, the acronym CCC refers to the hydrodynamic method of CCC.

Countercurrent Separation (CS). A general term that encompasses all modern forms of liquid-liquid separation techniques, including [HS]CCC and [F]CPC.

Elution Extrusion CCC (EECCC). A recently developed and fully parameterized CCC method (41) that takes advantage of the liquid nature of the stationary phase by combining classical elution and extrusion in a single run. EECCC allows coverage of the whole polarity range of analytes from $K_D = 0$ to $\infty$. After an initial elution stage, extrusion of the stationary phase is achieved by switching the supply of flowing liquid from the mobile phase to the originally stationary phase, while maintaining the centrifugal force through continued rotation. The point at which extrusion is begun (switch volume, $V_{CM}$), can be adjusted to optimize the resolution of target analytes and minimize the runtime. When $V_R$ is equal to $V_{CM} + V_C$ ($V_C$ being the total volume of the column), all analytes will have exited the column.

Extrusion. The process of pushing out the stationary phase portion of the CCC column. After performing classical elution for a certain period of time, the non-eluted analytes have migrated inside the column. Extrusion provides access to these analytes without the need to reach the elution volume, and can be achieved by pumping stationary phase into the column. The third stage of EECCC is called the extrusion stage.

GUESSmix. A mixture of commercially available natural products of certain size, polarity, and functional group composition, initially developed to provide a TLC-based method for the Generally Useful Estimation of Solvent Systems (G.U.E.S.S.) in CCC (44). In subsequent studies it has been used to evaluate solvent system performance.

Head. In hydrodynamic columns, the head is the end of the coil where the liquid is pushed by the Archimedean screw force when the machine rotor is spun, i.e., the higher pressure column side.

HEMWat. An array of biphasic solvent systems created by mixing various proportions of hexane, ethyl acetate, methanol and water; one example of a solvent system family.

High-Speed Countercurrent Chromatography (HSCCC). A hydrodynamic CCC system that uses a multilayer coil separation column and undergoes a type-J synchronous planetary motion.

Mobile Phase. In order to equilibrate a CCC system, the column is first filled with stationary phase, then the column is rotated and mobile phase is pumped into the column until mobile phase starts to elute. The mobile phase volume ($V_M$) remains constant throughout the classical elution stage of EECCC.

Multiple-Layer Countercurrent Chromatography (ML-CCC). Early variant of modern HSCCC instruments with columns that consist of multiples layers of coiled tubing.

Reciprocal Symmetry and Shifted Reciprocal Symmetry (ReS and ReSS) Plots. Graphical representations of CCC chromatograms capable of representing all K-values, zero to infinity. In ReS[S] plots, $K_D$ and $1/K_D$ are positioned on either side of a line of symmetry on the x-axis ($K_D$). ReS[S] plots demonstrate both the invertible and "symmetric" nature of CCC, a consequence of the exchange of the mobile and stationary phases by reversing the direction of the flow and the symmetry of the liquid-liquid partitioning process between two immiscible phases, respectively.

Liquid-liquid distribution ratio ($K_D$). The ratio of the concentration of an analyte in the stationary phase to its concentration in the mobile phase at equilibrium ($K^D)_A=[A]_{stationary}/[A]_{mobile}$). $K_D$ may also be represented by K or $K_c$. The retention volume ($V_R$) of an analyte follows the classical elution equation $V_R=V_M+K_D V_S$. The equation shows the relationship between $K_D$ and the experimentally measurable parameters of retention volume ($V_R$), mobile phase volume ($V_M$), and stationary phase volume ($V_S$). If a column is eluted only with mobile phase, it will theoretically take an infinite amount of time for an analyte that is exclusively soluble in the stationary phase ($K=\infty$) to exit the column. It shall be noted, that there is currently no generally accepted definition for the parameter that describes the partition/distribution behavior in CCC; an IUPAC definition is pending.

Partition Coefficient (K). The partition coefficient is the concentration of an analyte in the upper phase divided by the concentration of the same analyte in the lower phase of an equilibrated biphasic solvent system $(K)_A=[A]_{upper}/[A]_{lower}$).

Retention Volume ($V_R$). The volume at which a particular analyte elutes. Retention volumes are often calculated by multiplying the retention time and the flow rate, and are a necessary component of the liquid-liquid distribution ratio calculation.

Region of Optimal Resolution. See "Sweet Spot."

Solvent System. A mixture of liquids in defined proportions that forms two (or three) phases and can be used for CCC.

Solvent System Family. Biphasic solvent systems for CS applications have traditionally been organized as families that are comprised of the same solvents mixed in varying proportions. Common families are hexane-ethyl acetate-methanol-water (HEMWat, Table 1), chloroform-methanol-water (ChMWat), and heptane-ethyl acetate-methanol-water (the "Arizona" family). Solvent system families provide a methodical means of searching for a particular solvent system that predicts a reasonable $K_D$ value for the target compound(s) in CS.

Stationary Phase. Mobile phase is being pumped into the column while the stationary phase is held in the column, typically by centrifugal force. In order to equilibrate a countercurrent column, it is first filled with stationary phase, then the column is rotated and mobile phase is pumped into the column until mobile phase starts to elute. The stationary phase volume ($V_S$) remains constant throughout the classical elution stage of EECCC.

Stationary Phase Retention. The volume of stationary phase retained in the CCC column, $V_S$, is experimentally measured and compared with other columns using the dimensionless stationary phase volume ratio or stationary phase fraction parameter, $S_F: S_F=V_S/V_C$ ($V_C$=total column volume).

Sweep Elution. In EECCC, sweep elution is the second, intermediate stage of elution. After the switch volume ($V_{CM}$), the original stationary phase is pumped into the column while the original mobile phase is eluting until depleted ("swept").

Sweet Spot. Region of a countercurrent chromatogram or working area of a countercurrent separation that exhibits optimal resolution of the analytes. Optimal resolution refers to adequate separation between analytes so that the chromatogram is amenable to analyte identification.

Switch Volume ($V_{CM}$). Volume at which a CCC separation is switched from elution (CM=Classical Mode) to extrusion; see EECCC.

Tail. In hydrodynamic columns, the tail is the end of the coil opposite to the head. It is also the lower pressure column side; the pressure may even be negative inducing suction.

REFERENCES (1) Turner, A.; Chen, S. N.; Nikolic, D.; van Breemen, R.; Farnsworth, N. R.; Pauli, G. F. Coumaroyl iridoids and a depside from cranberry (*Vaccinium macrocarpon*). *J. Nat. Prod.* 2007, 70, 253-8.

(2) Fisher, D.; Garrard, I. J.; van den Heuvel, R.; Sutherland, I. A.; Chou, F. E.; Fahey, J. W. Technology transfer and scale up of a potential cancer-preventive plant dynamic extraction of glucoraphanin. *J. Liq. Chromatogr. Rel. Technol.* 2005, 28, 1913-22.

(3) Yanagida, A.; Shoji, A.; Shibusawa, Y.; Shindo, H.; Tagashira, M.; Ikeda, M.; Ito, Y. Analytical separation of tea catechins and food-related polyphenols by high-speed counter-current chromatography. *J. Chromatogr. A* 2006, 1112, 195-201.

(4) Degenhardt, A.; Hofmann, S.; Knapp, H.; Winterhalter, P. Preparative isolation of anthocyanins by high-speed countercurrent chromatography and application of the color activity concept to red wine. *J. Agric. Food Chem.* 2000, 48, 5812-8.

(5) Baderschneider, B.; Winterhalter, P. Isolation and characterization of novel stilbene derivatives from Riesling wine. *J. Agric. Food Chem.* 2000, 48, 2681-6.

(6) Baderschneider, B.; Winterhalter, P. Isolation and characterization of novel benzoates, cinnamates, flavonoids, and lignans from Riesling wine and screening for antioxidant activity. *J. Agric. Food Chem.* 2001, 49, 2788-98.

(7) Bonnlander, B.; Baderschneider, B.; Messerer, M.; Winterhalter, P. Isolation of two novel terpenoid glucose esters from Riesling wine. *J. Agric. Food Chem.* 1998, 46, 1474-8.

(8) Degenhardt, A.; Knapp, H.; Winterhalter, P. Rapid isolation of malvidin 3-glucoside from red wine by high speed countercurrent chromatography (HSCCC). *Vitis* 2000, 39, 43-4.

(9) Salas, E.; Duenas, M.; Schwarz, M.; Winterhalter, P.; Cheynier, W.; Fulcrand, H. Characterization of pigments from different high speed countercurrent chromatography wine fractions. *J. Agric. Food Chem.* 2005, 53, 4536-46.

(10) Schwarz, M.; Hofmann, G.; Winterhalter, P. Investigations on anthocyanins in wines from *Vitis vinifera* cv. pinotage: Factors influencing the formation of pinotin a and its correlation with wine age. *J. Agric. Food Chem.* 2004, 52, 498-504.

(11) Degenhardt, A.; Winterhalter, P. Isolation and purification of isoflavones from soy flour by high-speed countercurrent chromatography. *Eur. Food. Res. Technol.* 2001, 213, 277-80.

(12) Zanatta, C. F.; Cuevas, E.; Bobbio, F. O.; Winterhalter, P.; Mercadante, A. Z. Determination of anthocyanins from camu-camu (*Myrciaria dubia*) by HPLC-PDA, HPLC-MS, and NMR. *J. Agric. Food Chem.* 2005, 53, 9531-5.

(13) Vidal, S.; Hayasaka, Y.; Meudec, E.; Cheynier, W.; Skouroumounis, G. Fractionation of grape anthocyanin classes using multilayer coil countercurrent chromatography with step gradient elution. *J. Agric. Food Chem.* 2004, 52, 713-9.

(14) Hillebrand, S.; Schwarz, M.; Winterhalter, P. Characterization of anthocyanins and pyranoanthocyanins from blood orange [*Citrus sinensis* (L.) Osbeck] juice. *J. Agric. Food Chem.* 2004, 52, 7331-8.

(15) Schwarz, M.; Hillebrand, S.; Habben, S.; Degenhardt, A.; Winterhalter, P. Application of high-speed countercurrent chromatography to the large-scale isolation of anthocyanins. *Biochem. Eng. J.* 2003, 14, 179-89.

(16) Du, Q. Z.; Xu, Y. J.; Li, L.; Zhao, Y.; Jerz, G.; Winterhalter, P. Antioxidant constituents in the fruits of *Luffa cylindrica* (L.) Roem. *J. Agric. Food Chem.* 2006, 54, 4186-90.

(17) Degenhardt, A.; Engelhardt, U. H.; Wendt, A. S.; Winterhalter, P. Isolation of black tea pigments using high-speed countercurrent chromatography and studies on properties of black tea polymers. *J. Agric. Food Chem.* 2000, 48, 5200-5.

(18) He, J.; Ynag, R.; Zhou, T.; Rong, T.; Young, J. C.; Zhu, H.; Li, X.-Z.; Boland, G. J. Purification of deoxynivalenol from *Fusarium graminearum* rice culture and mouldy corn by high-speed counter-current chrmatography. *J. Chromatogr. A* 2007, 1151, 187-92.

(19) Grancher, D.; Jaussaud, P.; Durix, A.; Berthod, A.; Fenet, B.; Moulard, Y.; Bonnaire, Y.; Bony, S. Countercurrent chromatographic isolation of lolitrem B from endophyte-infected ryegrass (*Lolium perenne* L.) seed. *J. Chromatogr. A* 2004, 1059, 73-81.

(20) Rasooly, A.; Ito, Y. Toroidal coil Countercurrent Chromatography separation and analysis of staphylococcal enterotoxin a (SEA) in milk. *J. Liq. Chromatogr. Rel. Technol.* 1999, 22, 1285-93.

(21) Rasooly, A.; Ito, Y. Toroidal coil countercurrent chromatography separation of *Staphylococcus aureus* enterotoxin A in food. *J. Liq. Chromatogr. Rel. Technol.* 1998, 21, 93-102.

(22) Matsuda, S.; Matsuda, K.; Ito, Y. Separation of phospholipids and glycolipids using analytical toroidal-coil counter-current chromatography. II. Comparison of the hydrophobicity between Mycoplasma fermentans and human-brain lipids. *J. Liq. Chromatogr. Rel. Technol.* 2003, 26, 1135-47.

(23) Feger, W.; Brandauer, H.; Gabris, P.; Ziegler, H. Nonvolatiles of commercial lime and grapefruit oils separated by high-speed countercurrent chromatography. *J. Agric. Food Chem.* 2006, 54, 2242-52.

(24) Mayorga, H.; Knapp, H.; Winterhalter, P.; Duque, C. Glycosidically bound flavor compounds of cape gooseberry (*Physalis peruviana* L.). *J. Agric. Food Chem.* 2001, 49, 1904-8.

(25) Mayorga, H.; Duque, C.; Knapp, H.; Winterhalter, P. Hydroxyester disaccharides from fruits of cape gooseberry (*Physalis peruviana*). *Phytochemistry* 2002, 59, 439-45.

(26) Conway, W. D. *Countercurrent Chromatography: Apparatus, Theory & Applications*; VCH, 1990.

(27) Ito, Y. Golden rules and pitfalls in selecting optimum conditions for high-speed counter-current chromatography. *J. Chromatogr. A* 2005, 1065, 145-68.

(28) Berthod, A. *Countercurrent Chromatography: The Support-free Liquid Phase,* 1st ed.; Elsevier: Amsterdam; Boston, 2002; xxiv, 397 p.

(29) Oka, F.; Oka, H.; Ito, Y. Systematic search for suitable 2-phase solvent systems for high-speed countercurrent chromatography. *J. Chromatogr.* 1991, 538, 99-108.

(30) Foucault, A. P.; Chevolot, L. Counter-current chromatography: instrumentation, solvent selection and some recent applications to natural product purification. *J. Chromatogr. A* 1998, 808, 3-22.

(31) Schafer, K.; Winterhalter, P. Application of high speed countercurrent chromatography (HSCCC) to the isolation of kavalactones. *J. Liq. Chromatogr. Rel. Technol.* 2005, 28, 1703-16.

(32) Tsao, R.; Yang, R. Lutein in selected Canadian crops and agri-food processing by-products and purification by high-speed counter-current chromatography. *J. Chromatogr. A* 2006, 1112, 202-8.

(33) Long, L. J.; Song, Y.; Wu, J.; Lei, L.; Huang, K.; Long, B. W. Development of an efficient method for the preparative isolation and purification of chlorophyll a from a marine dinoflagellate *Amphidinium carterae* by high-speed counter-current chromatography coupled with reversed-phase high-performance liquid chromatography. *Anal. Bioanal. Chem.* 2006, 386, 2169-74.

(34) Booth, A. J.; Ngiam, S. H.; Lye, G. J. Antibiotic purification from fermentation broths by counter-current chromatography: analysis of product purity and yield tradeoffs. *Bioproc. Biosyst. Eng.* 2004, 27, 51-61.

(35) Ma, C. H.; Ke, W.; Sun, Z. L.; Peng, J. Y.; Li, Z. X.; Zhou, X.; Fan, G. R.; Huang, C. G. Large-scale isolation and purification of scoparone from *Herba artemisiae scopariae* by high-speed counter-current chromatography. *Chromatographia* 2006, 64, 83-7.

(36) Chen, L. J.; Song, H.; Lan, X. Q.; Games, D. E.; Sutherland, I. A. Comparison of high-speed counter-current chromatography instruments for the separation of the extracts of the seeds of *Oroxylum indicum*. *J. Chromatogr. A* 2005, 1063, 241-5.

(37) Peng, J. Y.; Fan, G. R.; Chai, Y. F.; Wu, Y. T. Efficient new method for extraction and isolation of three flavonoids from *Patrinia villosa* Juss. by supercritical fluid extraction and high-speed counter-current chromatography. *J. Chromatogr. A* 2006, 1102, 44-50.

(38) Yao, S.; Li, Y.; Kong, L. Y. Preparative isolation and purification of chemical constituents from the root of *Polygonum multiflorum* by high-speed counter-current chromatography. *J. Chromatogr. A* 2006, 1115, 64-71.

(39) Wei, Y.; Ito, Y. Preparative isolation of imperatorin, oxypeucedanin and isoimperatorin from traditional Chinese herb "bai zhi" Angelica dahurica (Fisch ex Hoffm) Benth. et Hook using multidimensional high-speed counter-current chromatography. J. Chromatogr. A 2006, 1115, 112-7.

(40) Ito, Y.; Sandlin, J. L.; Bowers, W. G. High-speed preparative countercurrent chromatography with a coil planet centrifuge. J. Chromatogr. 1982, 244, 247-58.

(41) Berthod, A.; Friesen, J. B.; Inui, T.; Pauli, G. F. Elution-extrusion countercurrent chromatography: Theory and concepts in metabolic analysis. Anal. Chem. 2007, 79, 3371-82.

(42) Friesen, J. B.; Pauli, G. F. Reciprocal symmetry plots as a representation of countercurrent chromatograms. Anal. Chem. 2007, 79, 2320-4.

(43) Friesen, J. B.; Pauli, G. F. Rational development of solvent system families in counter-current chromatography. J. Chromatogr. A 2007, 1151, 51-9.

(44) Friesen, J. B.; Pauli, G. F. G.U.E.S.S.—A generally useful estimate of solvent systems for CCC. J. Liq. Chromatogr. Rel. Technol. 2005, 28, 2777-806.

(45) Leo, A. J. Some advantages of calculating octanol water partition-coefficients. J. Pharm. Sci. 1987, 76, 166-8.

(46) Eltayar, N.; Tsai, R. S.; Vallat, P.; Altomare, C.; Testa, B. Measurement of partition-coefficients by various centrifugal partition chromatographic techniques—a comparative-evaluation. J. Chromatogr. 1991, 556, 181-94.

(47) Vallat, P.; Eltayar, N.; Testa, B.; Slacanin, I.; Marston, A.; Hostettmann, K. Centrifugal countercurrent chromatography, a promising means of measuring partition-coefficients. J. Chromatogr. 1990, 504, 411-9.

(48) Shibusawa, Y.; Shoji, A.; Yanagida, A.; Shindo, H. Determination of log P-o/w for catechins and their isomers, oligomers, and other organic compounds by stationary phase controlled high speed countercurrent chromatography. J. Liq. Chromatogr. Rel. Technol. 2005, 28, 2819-34.

(49) Berthod, A.; Carda-Broch, S. Determination of liquid-liquid partition coefficients by separation methods. J. Chromatogr. A 2004, 1037, 3-14.

(50) Berthod, A.; Ruiz-Angel, M. J.; Carda-Broch, S. Elution-extrusion countercurrent chromatography. Use of the liquid nature of the stationary phase to extend the hydrophobicity window. Anal. Chem. 2003, 75, 5886-94.

(51) Pan, Y. J.; Lu, Y. B. Recent progress in countercurrent chromatography. J. Liq. Chromatogr. Rel. Technol. 2007, 30, 649-79.

All references cited throughout this application, for example patent documents including issued or granted patents or equivalents; patent applications or publications; and non-patent literature documents or other source material are hereby incorporated by reference in their entireties, as though individually incorporated by reference, to the extent each reference is not inconsistent with the disclosure in this application (for example, a reference that is partially inconsistent is incorporated by reference except for the partially inconsistent portion of the reference).

Every formulation or combination of components described or exemplified herein can be used to practice the invention, unless otherwise stated. Whenever a range is given in the specification, for example a variable range or a concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein may be practiced in the absence of any element or elements, limitation or limitations which is not specifically disclosed herein.

One of ordinary skill in the art will appreciate that materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 1

The HEMWat Solvent System Family (see also 11/876,545 (156-07) filed Oct. 22, 2007).

| HEMWat System No. | Relative Proportions of Solvents | | | |
|---|---|---|---|---|
| | Hexane | EtOAc | Methanol | Water |
| −8 | 10 | 0 | 10 | 0 |
| −7 | 9 | 1 | 9 | 1 |
| −6 | 8 | 2 | 8 | 2 |
| −5 | 7 | 3 | 7 | 3 |
| −4 | 7 | 3 | 6 | 4 |
| −3 | 6 | 4 | 6 | 4 |
| −2 | 7 | 3 | 5 | 5 |
| −1 | 6 | 4 | 5 | 5 |
| 0 | 5 | 5 | 5 | 5 |
| +1 | 4 | 6 | 5 | 5 |
| +2 | 3 | 7 | 5 | 5 |
| +3 | 4 | 6 | 4 | 6 |
| +4 | 3 | 7 | 4 | 6 |
| +5 | 3 | 7 | 3 | 7 |
| +6 | 2 | 8 | 2 | 8 |
| +7 | 1 | 9 | 1 | 9 |
| +8 | 0 | 10 | 0 | 10 |

TABLE 2

Solvent system family map illustrating the whole range of $K_D$ values for 21 compounds in 17 different HEMWat solvent systems.

| $K_D$ intervals | $0 \leq K_D < 0.0625$ | $0.0625 \leq K_D < 0.125$ | $0.125 \leq K_D < 0.25$ | $0.25 \leq K_D < 0.5$ | $0.5 \leq K_D < 1$ | $1 \leq K_D < 2$ | $2 \leq K_D < 4$ | $4 \leq K_D < 8$ | $8 \leq K_D < 16$ | $16 \leq K_D < 32$ | $32 \leq K_D < \infty$ |
|---|---|---|---|---|---|---|---|---|---|---|---|
| −8 | rXHTDC GRFQUA VNMEZ | | | | DI | Y | | | | | b |
| −7 | rXHTDC GRFQUA VNE | | MZ | | O | I | | Y | | | b |
| −6 | rXHTDC GRFQUA VNE | | MZ | | | O | I | | | | Yb |
| −5 | rXHTDC GRAV | FQUINE | | MZ | | | O | B | | | Yb |
| −4 | rXHTDC GR | AVFQU | NE | M | Z | | O | | I | | Yb |
| −3 | rXHTDC GR | FQU | AVN | E | MZ | | O | | I | | Yb |
| −2 | rXHTDC GR | FQU | AVN | | ME | Z | O | | I | | Yb |
| −1 | rXHTDC G | | RFQU | AVN | | MEZ | | O | | I | Yb |
| 0 | rXHTG | DR | CF | QUAV | S | ME | Z | O | | I | Yb |
| +1 | rXHT | | GRDC | F | QUAV | NM | EZ | O | | I | Yb |
| +2 | r | XHT | | DCG | SP | QUAV | MPEZ | O | | I | Yb |
| +3 | r | XHT | | DCG | RF | QUAV | M | MEZ | | O | IYb |
| +4 | rXHT | FQU | | DCG | | RFG | GAP | NMEZ | | O | IYb |
| +5 | r | XHT | | DC | O | RFVAV | M | | | QZ | NEOIYb |
| +6 | r | XHT | | D | CG | F | | RUAY | M | Z | QNEO IYb |
| +7 | r | XHT | | D | CG | F | | | RUAY | MZ | QNEO IYb |
| +8 | rXHT | | | D | CG | | | | FRUA VM | | Z QNEO IYb |

We claim:

1. A method of visualization of one or more analytes detected by a liquid-liquid chromatographic instrument, said method comprising:
   detecting said one or more analyte by said liquid-liquid chromatographic instrument;
   providing a data set comprising a plurality of data points corresponding to one or more analytes detected by said detecting step, wherein said data points comprise at least one parameter related to a K-value or a parameter from which a K-value can be determined;
   calculating said K-value for at least a portion of said data set;
   transforming a portion of said K-values from said calculating step by a reciprocal transformation to generate output data comprising a transformed K-value, wherein said transformed K-value is a real number for all K ranging from zero to infinity;
   selecting a symmetry midline value, M; wherein in said transforming step, for K greater than or equal to M, said x-coordinate has a value x, wherein $x=2M-M^2/K$, and for K less than M, x=K, thereby generating said output data that is a reciprocal shifted symmetry visualization; and providing said output data to a user in a single chromatogram;

wherein said output data is provided to a user in a graphical form, wherein said graphical from is obtained by:
plotting onto a X-Y coordinate system said transformed K-value and any untransformed K-value as a x-coordinate of the X-Y coordinate system; and
plotting a parameter related to said analyte relative amount as a y-coordinate of said X-Y coordinate system.

2. The method of claim 1, wherein M=1.

3. The method of claim 1, wherein M is selected to have a value that is within an optimum resolution range of said instrument.

4. The method of claim 1, wherein M has a value that is selected from a range that is greater than or equal to 0.001 and less than or equal to 1000.

5. The method of claim 1, wherein said liquid-liquid chromatographic instrument is a partition chromatography instrument.

6. The method of claim 1, wherein said liquid-liquid chromatographic instrument is a counter-current chromatographic instrument.

7. The method of claim 1, wherein said liquid-liquid chromatographic instrument has an operating mode selected from the group consisting of: normal mode, dual mode, elution-extrusion counter-current chromatography, back extrusion counter-current chromatography, gradient mode, and pH zone refinement mode.

8. The method of claim 1, wherein said K-value is a $K_D$ value.

9. The method of claim 1, wherein x=2M−1/K.

10. The method of claim 1, wherein the displaying step comprises one or more of a visual display, electronic storage media, or hard-copy print-out.

11. The method of claim 1, wherein the data set is collected from said liquid-liquid chromatographic instrument in real-time.

12. The method of claim 1, further comprising repeating each of said steps to obtain a second output data from a second liquid-liquid chromatographic instrument; and
comparing said second output data to said output data to determine an instrument performance parameter for at least one of said liquid-liquid chromatographic instrument.

13. The method of claim 12, wherein said instrument performance parameter is selected from the group consisting of: analyte peak sharpness, analyte peak magnitude, absence or presence of one or more analyte peaks, an analyte K-value, analyte peak symmetry, peak resolution, and solvent system parameter.

14. The method of 13, wherein said one or more analytes comprises one or more components selected from those shown in FIG. 5.

15. The method of claim 1, further comprising calibrating said liquid-liquid chromatographic instrument by:
introducing one or more reference analytes to said liquid-liquid chromatographic instrument to generate said output data;
providing a reference output data comprising said one or more reference analytes;
comparing a parameter from said output data to a reference parameter from said reference output data; and
selectively adjusting one or more instrument parameters so that said parameter from said output data substantially corresponds to said reference parameter.

16. The method of claim 15, wherein said instrument parameter is a physical parameter of said instrument, said physical parameter selected from the group consisting of:
dimension of a container that constrains said liquid-liquid solvent system; centrifugation parameter; coil geometry; coil material; cell flowpath geometry; cell flowpath material; active volume dimension; and dead volume dimension.

17. The method of claim 1, wherein the at least one parameter related to a K-value is a volume parameter, and K is calculated as $K=(V_R-V_M)/V_S$
wherein $V_R$ is retention volume, $V_M$ is mobile phase volume, and $V_s$ is stationary phase volume.

* * * * *

UNITED STATES PATENT AND TRADEMARK OFFICE
CERTIFICATE OF CORRECTION

PATENT NO.         : 8,175,817 B2
APPLICATION NO.    : 11/961026
DATED              : May 8, 2012
INVENTOR(S)        : Pauli et al.

It is certified that error appears in the above-identified patent and that said Letters Patent is hereby corrected as shown below:

On the title page 2, item [56]; in the list of OTHER PUBLICATIONS, please replace "El Tayer e3t al." with --El Tayer et al.--.

In claim 1, column 33, line 7, please replace "graphical from" with --graphical form--.

Please cancel claim 9.

Signed and Sealed this
Thirtieth Day of October, 2012

David J. Kappos
*Director of the United States Patent and Trademark Office*